US012646963B2

(12) United States Patent
Valentine

(10) Patent No.: US 12,646,963 B2
(45) Date of Patent: Jun. 2, 2026

(54) CHARGER FOR A VAPORIZER DEVICE

(71) Applicant: JUUL Labs, Inc., San Francisco, CA (US)

(72) Inventor: Val Valentine, San Francisco, CA (US)

(73) Assignee: JUUL Labs, Inc., San Francisco, CA (US)

( * ) Notice: Subject to any disclaimer, the term of this patent is extended or adjusted under 35 U.S.C. 154(b) by 799 days.

(21) Appl. No.: 17/962,351

(22) Filed: Oct. 7, 2022

(65) Prior Publication Data

US 2023/0043830 A1     Feb. 9, 2023

Related U.S. Application Data

(63) Continuation of application No. PCT/US2021/026406, filed on Apr. 8, 2021.

(60) Provisional application No. 63/007,312, filed on Apr. 8, 2020.

(51) Int. Cl.
| | |
|---|---|
| *H02J 7/00* | (2026.01) |
| *A24F 40/40* | (2020.01) |
| *A24F 40/50* | (2020.01) |
| *A24F 40/70* | (2020.01) |
| *H02J 7/96* | (2026.01) |

(52) U.S. Cl.
CPC .............. *H02J 7/96* (2026.01); *A24F 40/40* (2020.01); *A24F 40/50* (2020.01); *A24F 40/70* (2020.01); *A61M 2205/8206* (2013.01)

(58) Field of Classification Search
None
See application file for complete search history.

(56) References Cited

U.S. PATENT DOCUMENTS

| | | | |
|---|---|---|---|
| 5,865,185 | A | 2/1999 | Collins et al. |
| 6,326,097 | B1 | 12/2001 | Hockaday |
| 8,820,330 | B2 | 9/2014 | Bellinger et al. |
| 8,833,364 | B2 | 9/2014 | Buchberger |
| 9,099,873 | B2 | 8/2015 | Xiang |
| 9,131,733 | B2 | 9/2015 | Liu |
| 9,240,695 | B2 | 1/2016 | Xiang |
| 9,240,697 | B2 | 1/2016 | Xiang |
| 9,281,705 | B2 | 3/2016 | Xiang |
| 9,350,181 | B2 | 5/2016 | Xiang |
| 9,385,554 | B2 | 7/2016 | Xiang |
| 9,423,152 | B2 | 8/2016 | Ampolini et al. |
| 9,438,049 | B2 | 9/2016 | Xiang |
| 9,455,579 | B2 | 9/2016 | Xiang |
| 9,465,081 | B2 | 10/2016 | Xiang |
| 9,502,917 | B2 | 11/2016 | Nishihara et al. |
| 9,504,278 | B2 | 11/2016 | Katabi et al. |

(Continued)

FOREIGN PATENT DOCUMENTS

| | | |
|---|---|---|
| CN | 202722502 U | 2/2013 |
| CN | 203152489 U | 8/2013 |

(Continued)

*Primary Examiner* — Arun C Williams
(74) *Attorney, Agent, or Firm* — Mintz Levin Cohn Ferris Glovsky and Popeo, P.C.

(57) ABSTRACT

A charging system for charging a vaporizer device is described. The charger may be adapted to control the output voltage to the vaporizer device, thus improving charging efficiency and reducing waste heat generation. Related systems, methods, and articles of manufacture are also described.

21 Claims, 15 Drawing Sheets

(56) References Cited

U.S. PATENT DOCUMENTS

| | | | |
|---|---|---|---|
| 9,573,751 B2 | 2/2017 | Liu | |
| 9,655,383 B2 | 5/2017 | Holzherr et al. | |
| 9,682,800 B2 | 6/2017 | Xiang | |
| 9,781,953 B2 | 10/2017 | Verleur et al. | |
| 9,974,338 B2 | 5/2018 | Alarcon et al. | |
| 9,985,455 B2 | 5/2018 | Alarcon et al. | |
| 10,034,988 B2 | 7/2018 | Wensley et al. | |
| 10,039,322 B2 | 8/2018 | Schiff et al. | |
| 10,058,122 B2 | 8/2018 | Steingraber et al. | |
| 10,064,434 B2 | 9/2018 | Zitzke et al. | |
| 10,069,320 B2 | 9/2018 | Cai et al. | |
| 10,090,693 B2 | 10/2018 | Alarcon | |
| 10,098,383 B2 | 10/2018 | Alarcon et al. | |
| 10,172,392 B2 | 1/2019 | Sur et al. | |
| 10,201,186 B2 | 2/2019 | Alarcon et al. | |
| 10,206,431 B2 | 2/2019 | Sur et al. | |
| 10,218,193 B2 | 2/2019 | Gratton | |
| 10,226,077 B2 | 3/2019 | Matsumoto et al. | |
| 10,276,898 B2 | 4/2019 | Leadley | |
| 10,321,718 B2 | 6/2019 | Qiu | |
| 10,439,419 B2 | 10/2019 | Bernauer et al. | |
| 10,470,495 B2 | 11/2019 | Sur et al. | |
| 10,492,533 B2 | 12/2019 | Bernauer et al. | |
| 10,505,383 B2 | 12/2019 | Sur | |
| 10,517,326 B2 | 12/2019 | Sur et al. | |
| 10,524,509 B2 | 1/2020 | Sur et al. | |
| 10,537,135 B2 | 1/2020 | Smith et al. | |
| 10,537,137 B2 | 1/2020 | Sur et al. | |
| 10,548,349 B2 | 2/2020 | Sur | |
| 10,561,807 B2 | 2/2020 | Yamada et al. | |
| 10,588,356 B2 | 3/2020 | Harrison et al. | |
| 10,653,179 B2 | 5/2020 | Matsumoto et al. | |
| 10,736,359 B2 | 8/2020 | Verleur et al. | |
| 10,750,779 B2 | 8/2020 | Schennum et al. | |
| 10,757,972 B2 | 9/2020 | Matsumoto et al. | |
| 10,770,913 B2 | 9/2020 | Schennum et al. | |
| 10,806,180 B2 | 10/2020 | Otiaba | |
| 10,827,783 B2 | 11/2020 | Sur | |
| 10,881,131 B2 | 1/2021 | Matsumoto et al. | |
| 10,888,125 B2 | 1/2021 | Anderson et al. | |
| 10,966,460 B2 | 4/2021 | Frisbee et al. | |
| 10,986,875 B2 | 4/2021 | Fisher et al. | |
| 11,039,645 B2 | 6/2021 | Sur | |
| 11,094,993 B2 | 8/2021 | Sur | |
| 11,147,316 B2 | 10/2021 | Farine et al. | |
| 11,160,314 B2 | 11/2021 | Watanabe et al. | |
| 11,202,342 B2 | 12/2021 | Takeuchi et al. | |
| 11,590,296 B2 | 2/2023 | Hatton et al. | |
| 11,606,970 B2 | 3/2023 | Fu et al. | |
| 2005/0285538 A1 | 12/2005 | Jaworski et al. | |
| 2008/0315829 A1 | 12/2008 | Jones et al. | |
| 2011/0040235 A1 | 2/2011 | Castel | |
| 2014/0020697 A1 | 1/2014 | Liu | |
| 2014/0062417 A1 | 3/2014 | Li et al. | |
| 2014/0123989 A1 | 5/2014 | Lamothe | |
| 2014/0190496 A1 | 7/2014 | Wensley et al. | |
| 2014/0202474 A1 | 7/2014 | Peleg et al. | |
| 2014/0299137 A1 | 10/2014 | Kieckbusch et al. | |
| 2014/0373857 A1 | 12/2014 | Steinberg | |
| 2015/0027472 A1 | 1/2015 | Amir | |
| 2015/0102777 A1 | 4/2015 | Cooper | |
| 2015/0136158 A1 | 5/2015 | Stevens et al. | |
| 2015/0164138 A1 | 6/2015 | Liu | |
| 2015/0173124 A1 | 6/2015 | Qiu | |
| 2015/0216237 A1 | 8/2015 | Wensley et al. | |
| 2015/0237918 A1 | 8/2015 | Liu | |
| 2015/0257447 A1 | 9/2015 | Sullivan | |
| 2015/0272223 A1 | 10/2015 | Weigensberg et al. | |
| 2015/0280273 A1 | 10/2015 | Liu | |
| 2015/0305409 A1 | 10/2015 | Verleur et al. | |
| 2015/0333542 A1 | 11/2015 | Alarcon et al. | |
| 2015/0366266 A1 | 12/2015 | Chen | |
| 2016/0113326 A1 | 4/2016 | Li et al. | |
| 2016/0213065 A1 | 7/2016 | Wensley et al. | |
| 2016/0226286 A1 | 8/2016 | Xiang | |
| 2016/0227840 A1 | 8/2016 | Xiang | |
| 2016/0262443 A1 | 9/2016 | Piccirilli et al. | |
| 2016/0278435 A1 | 9/2016 | Choukroun et al. | |
| 2016/0295922 A1 | 10/2016 | John et al. | |
| 2016/0345627 A1 | 12/2016 | Liu | |
| 2016/0345628 A1 | 12/2016 | Sabet | |
| 2016/0353800 A1* | 12/2016 | Di Carlo ................ A24F 40/30 | |
| 2017/0013875 A1 | 1/2017 | Schennum et al. | |
| 2017/0042248 A1 | 2/2017 | Xiang | |
| 2017/0112196 A1 | 4/2017 | Sur et al. | |
| 2017/0119052 A1 | 5/2017 | Williams et al. | |
| 2017/0143043 A1 | 5/2017 | Liu | |
| 2017/0150756 A1 | 6/2017 | Rexroad et al. | |
| 2017/0215470 A1 | 8/2017 | Piccirilli et al. | |
| 2017/0215484 A1 | 8/2017 | Xiang | |
| 2017/0250552 A1 | 8/2017 | Liu | |
| 2017/0294804 A1 | 10/2017 | Sur | |
| 2017/0303597 A1 | 10/2017 | Tsui | |
| 2018/0098574 A1 | 4/2018 | Sur et al. | |
| 2018/0271155 A1 | 9/2018 | Baker et al. | |
| 2019/0021400 A1 | 1/2019 | Fornarelli | |
| 2019/0200677 A1 | 7/2019 | Chong et al. | |
| 2019/0208824 A1 | 7/2019 | Wright | |
| 2019/0280486 A1 | 9/2019 | Cheng et al. | |
| 2019/0387791 A1 | 12/2019 | Pierce et al. | |
| 2020/0000143 A1 | 1/2020 | Anderson et al. | |
| 2020/0046025 A1 | 2/2020 | Otiaba et al. | |
| 2020/0187560 A1 | 6/2020 | Trzecieski | |
| 2020/0221778 A1 | 7/2020 | Trzecieski | |
| 2021/0015158 A1 | 1/2021 | Moloney et al. | |
| 2021/0153562 A1 | 5/2021 | Fishwick et al. | |

FOREIGN PATENT DOCUMENTS

| | | |
|---|---|---|
| CN | 102754924 B | 9/2014 |
| CN | 102970885 B | 5/2015 |
| CN | 104102143 B | 5/2015 |
| CN | 105658100 A | 6/2016 |
| CN | 106136324 A | 11/2016 |
| CN | 206462409 U | 9/2017 |
| CN | 105357995 B | 8/2018 |
| CN | 109588779 A | 4/2019 |
| CN | 104621717 B | 7/2019 |
| CN | 105208882 B | 7/2019 |
| CN | 106102811 B | 3/2020 |
| DE | 212017000291 U1 | 9/2019 |
| DE | 102019117231 B4 | 6/2022 |
| EP | 3007305 A1 | 4/2016 |
| EP | 3026779 A1 | 6/2016 |
| EP | 3322311 B1 | 5/2018 |
| EP | 3016233 B1 | 6/2018 |
| EP | 3365051 B1 | 11/2019 |
| EP | 3518377 B1 | 5/2020 |
| EP | 3510649 B1 | 10/2020 |
| EP | 3612044 B1 | 12/2020 |
| EP | 3547859 B1 | 3/2021 |
| EP | 3424353 B1 | 4/2021 |
| EP | 3549235 B1 | 5/2021 |
| EP | 3646744 B1 | 5/2021 |
| EP | 3674732 B1 | 9/2021 |
| EP | 3607840 B1 | 11/2021 |
| EP | 3646743 B1 | 3/2022 |
| EP | 3581039 B1 | 6/2022 |
| EP | 3674729 B1 | 6/2022 |
| EP | 3698658 B1 | 7/2022 |
| EP | 3541213 B1 | 11/2022 |
| EP | 3586654 B1 | 11/2022 |
| EP | 3820319 B1 | 3/2023 |
| GB | 2566856 B | 6/2019 |
| GB | 2566857 B | 8/2019 |
| GB | 2587745 B | 8/2021 |
| KR | 20-0470584 Y1 | 12/2013 |
| KR | 10-1570876 B1 | 11/2015 |
| TW | 202018490 A | 5/2020 |
| WO | WO-2008077271 A1 | 7/2008 |
| WO | WO-2014020953 A1 | 2/2014 |
| WO | WO-2014194499 A1 | 12/2014 |
| WO | WO-2014206148 A1 | 12/2014 |
| WO | WO-2015021658 A1 | 2/2015 |

(56)     References Cited

FOREIGN PATENT DOCUMENTS

| WO | WO-2015035689 A1 | 3/2015 |
| WO | WO-2015054961 A1 | 4/2015 |
| WO | WO-2015107551 A2 | 7/2015 |
| WO | WO-2015109618 A1 | 7/2015 |
| WO | WO-2015137815 A1 | 9/2015 |
| WO | WO-2015157928 A1 | 10/2015 |
| WO | WO-2015168828 A1 | 11/2015 |
| WO | WO-2015190810 A1 | 12/2015 |
| WO | WO-2016000207 A1 | 1/2016 |
| WO | WO-2016008067 A1 | 1/2016 |
| WO | WO-2016008096 A1 | 1/2016 |
| WO | WO-2016026156 A1 | 2/2016 |
| WO | WO-2016029382 A1 | 3/2016 |
| WO | WO-2016029464 A1 | 3/2016 |
| WO | WO-2016095206 A1 | 6/2016 |
| WO | WO-2016154900 A1 | 10/2016 |
| WO | WO-2016202028 A1 | 12/2016 |
| WO | WO-2017024477 A1 | 2/2017 |
| WO | WO-2017056103 A1 | 4/2017 |
| WO | WO-2017063256 A1 | 4/2017 |
| WO | WO-2017067326 A1 | 4/2017 |
| WO | WO-2017075827 A1 | 5/2017 |
| WO | WO-2017091926 A1 | 6/2017 |
| WO | WO-2018087738 A1 | 5/2018 |
| WO | WO-2020061527 A1 | 3/2020 |
| WO | WO-2020132127 A1 | 6/2020 |
| WO | WO-2021113533 A1 | 6/2021 |

* cited by examiner

170

CHARGER FOR A VAPORIZER DEVICE

CROSS REFERENCE TO RELATED APPLICATION

This application claims priority to PCT Application No. PCT/US21/26406 filed on Apr. 8, 2021 which claims priority to U.S. Provisional Application No. 63/007,312, entitled "CHARGER FOR A VAPORIZER DEVICE" and filed on Apr. 8, 2020, the disclosure of which is incorporated herein by reference in its entirety.

TECHNICAL FIELD

The subject matter described herein relates to vaporizer devices, including a charging device for a vaporizer device.

BACKGROUND

Vaporizer devices, which can also be referred to as vaporizers, electronic vaporizer devices, or e-vaporizer devices, can be used for delivery of an aerosol (for example, a vapor-phase and/or condensed-phase material suspended in a stationary or moving mass of air or some other gas carrier) containing one or more active ingredients by inhalation of the aerosol by a user of the vaporizing device. For example, electronic nicotine delivery systems (ENDS) include a class of vaporizer devices that are battery powered and that can be used to simulate the experience of smoking, but without burning of tobacco or other substances. Vaporizers are gaining increasing popularity both for prescriptive medical use, in delivering medicaments, and for consumption of tobacco, nicotine, and other plant-based materials. Vaporizer devices can be portable, self-contained, and/or convenient for use.

In use of a vaporizer device, the user inhales an aerosol, colloquially referred to as "vapor," which can be generated by a heating element that vaporizes (e.g., causes a liquid or solid to at least partially transition to the gas phase) a vaporizable material, which can be liquid, a solution, a solid, a paste, a wax, and/or any other form compatible for use with a specific vaporizer device. The vaporizable material used with a vaporizer can be provided within a cartridge for example, a separable part of the vaporizer device that contains vaporizable material) that includes an outlet (for example, a mouthpiece) for inhalation of the aerosol by a user.

To receive the inhalable aerosol generated by a vaporizer device, a user may, in certain examples, activate the vaporizer device by taking a puff, by pressing a button, and/or by some other approach. A puff as used herein can refer to inhalation by the user in a manner that causes a volume of air to be drawn into the vaporizer device such that the inhalable aerosol is generated by a combination of the vaporized vaporizable material with the volume of air.

An approach by which a vaporizer device generates an inhalable aerosol from a vaporizable material involves heating the vaporizable material in a vaporization chamber (e.g., a heater chamber) to cause the vaporizable material to be converted to the gas (or vapor) phase. A vaporization chamber can refer to an area or volume in the vaporizer device within which a heat source (for example, a conductive, convective, and/or radiative heat source) causes heating of a vaporizable material to produce a mixture of air and vaporized material to form a vapor for inhalation of the vaporizable material by a user of the vaporization device.

In some implementations, the vaporizable material can be drawn out of a reservoir and into the vaporization chamber via a wicking element (e.g., a wick). Drawing of the vaporizable material into the vaporization chamber can be at least partially due to capillary action provided by the wick as the wick pulls the vaporizable material along the wick in the direction of the vaporization chamber.

Vaporizer devices can be controlled by one or more controllers, electronic circuits (for example, sensors, heating elements), and/or the like on the vaporizer. Vaporizer devices can also wirelessly communicate with an external controller for example, a computing device such as a smartphone).

SUMMARY

In certain aspects of the current subject matter, challenges associated with charging a vaporizer device can be addressed by inclusion of one or more of the features described herein or comparable/equivalent approaches as would be understood by one of ordinary skill in the art. Aspects of the current subject matter relate to a system for charging a battery in a vaporizer device.

In one aspect, there is provided a method for charging a vaporizer device. The method may include: receiving, at a charging device providing an input voltage to a vaporizer device, data indicating a voltage associated with a battery of the vaporizer device; and outputting, to the vaporizer device, power at an output voltage determined based at least in part on the data indicating the voltage associated with the battery of the vaporizer device.

In some variations, one or more of the following features may optionally be included in any feasible combination. The data indicating the voltage of associated with the battery of the vaporizer device may include one or more indicators of a current voltage of the battery.

In some variations, the method may further include: determining, by the charging device, a difference between the input voltage at the vaporizer device and the current voltage of the battery of the vaporizer device; and in response to determining that the difference is below a threshold voltage, setting, by the charging device, the input voltage of the vaporizer device to be at least the threshold voltage greater than the current voltage of the battery of the vaporizer device.

In some variations, the threshold voltage may be from 0.05 volts to 0.2 volts.

In some variations, the threshold voltage may be 0.1 volts.

In some variations, the data indicating the voltage of associated with the battery of the vaporizer device may include one or more indicators of a desired voltage requested by the vaporizer device. The desired voltage requested by the vaporizer device may be a threshold voltage above a current voltage of the battery of the vaporizer device.

In some variations, the method may further include: detecting that the vaporizer device is coupled with the charging device; and in response to detecting that the vaporizer device is coupled with the charging device, determining, by the charging device, whether the battery of the vaporizer device requires charging. The charging device may output power to the vaporizer device in response to determining that the vaporizer device requires charging. In some variations, the charging device may determine that the battery of the vaporizer device requires charging based on at least a current flowing to the vaporizer device being above a threshold current. In some variations, the vaporizer device and the charging device may be coupled via a serial communication system. The data indicating the voltage associated with the battery of the vaporizer device may be transmitted from the vaporizer device to the charging device via the serial communication system. In some variations, the serial communication system may be a universal asynchronous receiver transmitter system including a transmitter pin and a receiver pin.

In some variations, the data indicating the voltage associated with the battery of the vaporizer device may be transmitted via one or more charging contacts at the vaporizer device and one or more corresponding charging contacts at the charging device.

In some variations, the method may further include: in response to a current flowing to the vaporizer device being below a threshold current, setting, by the charging device, the input voltage of the vaporizer device below a minimum voltage of the battery of the vaporizer device for communicating the data indicating the voltage of the battery of the vaporizer device.

In some variations, the method may further include: determining, by the charging device, whether to stop charging the battery of the vaporizer device; in response to determining that charging of the battery of the vaporizer device will be stopped, discontinuing, by the charging device, the outputting of power to the vaporizer device; and in response to determining that charging of the vaporizer device will continue, continuing to output, by the charging device, the power to the vaporizer device.

In some variations, the charging device may be a power bank, a portable charging case, or a charging adapter.

In another aspect, there is provided an apparatus. The apparatus may include a controller configured to at least: receive data indicating a voltage associated with a battery of a vaporizer device; and output, to the vaporizer device, power at an output voltage determined based at least in part on the data indicating the voltage associated with the battery of the vaporizer device.

In some variations, one or more of the following features may optionally be included in any feasible combination. The data indicating the voltage associated with the battery of the vaporizer device may include one or more indicators of a current voltage of the battery.

In some variations, the controller may be further configured to at least: determine a difference between an input voltage at the vaporizer device and the current voltage of the battery of the vaporizer device; and in response to determining that the difference is below a threshold voltage, set the input voltage of the vaporizer device to be at least the threshold voltage greater than the current voltage of the battery of the vaporizer device.

In some variations, the threshold voltage may be 0.05 volts to 0.2 volts.

In some variations, the threshold voltage may be 0.1 volts.

In some variations, the data indicating the voltage of associated with the battery of the vaporizer device may include one or more indicators of a desired voltage requested by the vaporizer device. The desired voltage requested by the vaporizer device may be a threshold voltage above a current voltage of the battery of the vaporizer device.

In some variations, the controller may be further configured to: detect that the vaporizer device is coupled with the apparatus; and in response to detecting that the vaporizer device is coupled with the apparatus, determine whether the battery of vaporizer device requires charging. The apparatus may output power to the vaporizer device in response to determining that the vaporizer device requires charging.

In some variations, the apparatus may determine that the vaporizer device requires charging based at least on a current flowing to the vaporizer device being above a threshold current.

In some variations, the vaporizer device and the apparatus may be coupled via a serial communication system. The data indicating the voltage associated with the battery of the vaporizer device may be transmitted from the vaporizer device to the apparatus via the serial communication system.

In some variations, the serial communication system may be a universal asynchronous receiver transmitter system including a transmitter pin and a receiver pin.

In some variations, the data indicating the voltage associated with the battery of the vaporizer device may be transmitted via one or more charging contacts at the vaporizer device and one or more corresponding charging contacts at the apparatus.

In some variations, the controller may be further configured to respond to a current flowing to the vaporizer device being below a threshold current by at least setting an input voltage of the vaporizer device below a minimum voltage of the battery of the vaporizer device for communicating the data indicating the voltage of the battery of the vaporizer device.

In some variations, the controller may be further configured to: determine whether to stop charging the vaporizer device; in response to determining that charging of the vaporizer device will be stopped, discontinue the output of power to the vaporizer device; and in response to determining that charging of the vaporizer device will continue, continue to output power to the vaporizer device.

In some variations, the apparatus may be a power bank, a portable charging case, or a charging adapter.

In another aspect, there is provided a charging device that includes a power source, at least one charging contact, and a controller coupled to the power source and the at least one charging contact. The controller may be configured to: receive, from an electronic device and via the at least one charging contact, data indicating a voltage associated with a battery of the electronic device, and output, to the electronic device and via the at least one charging contact, power at an output voltage that is based on the voltage associated with the battery of the electronic device.

In some variations, one or more of the following features may optionally be included in any feasible combination. The electronic device may be a vaporizer device.

In some variations, the voltage associated with the battery of the electronic device may include a current voltage of the battery of the electronic device. The controller may be further configured to determine the output voltage by adding a voltage differential to the current voltage of the battery.

In some variations, the voltage associated with the battery of the electronic device may include a voltage requested by the electronic device in order to charge the battery. The controller may be further configured to modify, based on the voltage associated with the battery of the electronic device, a boost level applied to a voltage of the power source in order to generate the output voltage.

In some variations, the voltage associated with the battery may be less than 5V.

In another aspect, there is provided a vaporizer device including a battery, at least one charging contact, and a controller coupled to the battery and the at least one charging contact. The controller may be configured to at least: transmit, to a charging device and via the at least one charging contact, data indicating a voltage associated with the battery, receive, from the charging device and via the at least one charging contact, power at an input voltage that is based on the voltage associated with the battery, and charge the battery with the power.

In some variations, the voltage associated with the battery may include a current voltage of the battery. The controller may be further configured to determine the voltage associated with the battery by adding a voltage differential to a current voltage of the battery.

In some variations, the voltage associated with the battery may include a voltage requested by the controller in order to charge the battery.

In some variations, the voltage associated with the battery may be less than 5 volts.

The details of one or more variations of the subject matter described herein are set forth in the accompanying drawings and the description below. Other features and advantages of the subject matter described herein will be apparent from the description and drawings, and from the claims. The claims that follow this disclosure are intended to define the scope of the protected subject matter.

BRIEF DESCRIPTION OF THE DRAWINGS

The accompanying drawings, which are incorporated into and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1A:
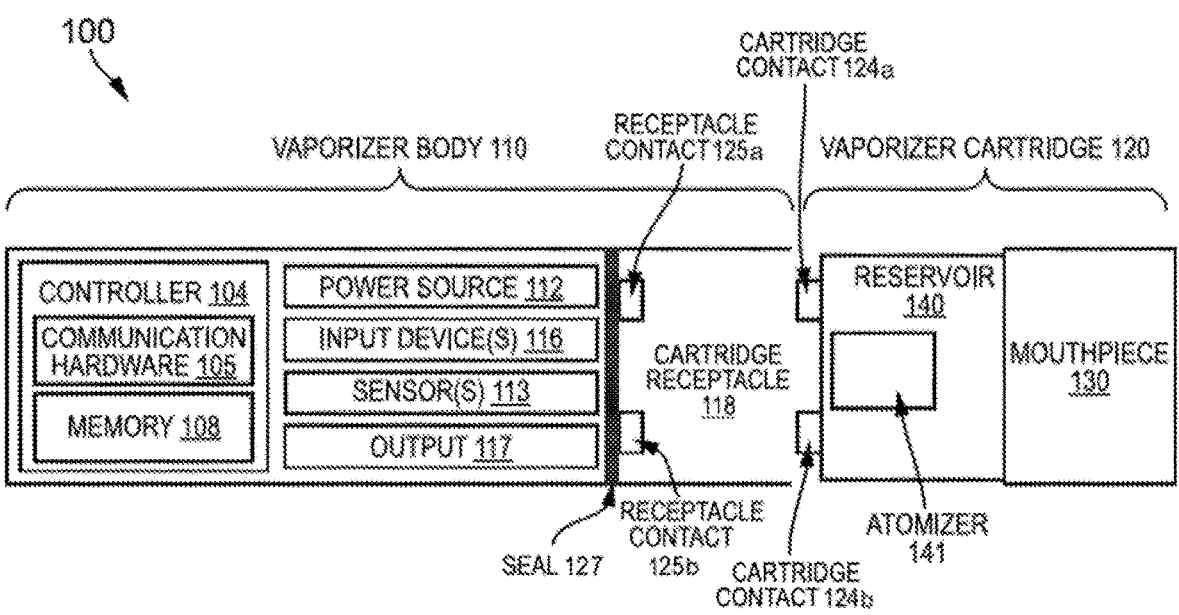
FIG. 1A depicts a block diagram illustrating an example of a vaporizer device consistent with implementations of the current subject matter.

Implementations of the current subject matter include methods, apparatuses, articles of manufacture, and systems relating to vaporization of one or more materials for inhalation by a user. Example implementations include vaporizer devices and systems including vaporizer devices. The term "vaporizer device" as used in the following description and claims refers to any of a self-contained apparatus, an apparatus that includes two or more separable parts (for example, a vaporizer body that includes a battery and other hardware, and a cartridge that includes a vaporizable material), and/or the like. A "vaporizer system," as used herein, can include one or more components, such as a vaporizer device. Examples of vaporizer devices consistent with implementations of the current subject matter include electronic vaporizers, electronic nicotine delivery systems (ENDS), and/or the like. In general, such vaporizer devices are hand-held devices that heat (such as by convection, conduction, radiation, and/or some combination thereof) a vaporizable material to provide an inhalable dose of the material. The vaporizable material used with a vaporizer device can be provided within a cartridge (for example, a part of the vaporizer that contains the vaporizable material in a reservoir or other container) which can be refillable when empty, or disposable such that a new cartridge containing additional vaporizable material of a same or different type can be used). A vaporizer device can be a cartridge-using vaporizer device, a cartridge-less vaporizer device, or a multi-use vaporizer device capable of use with or without a cartridge. For example, a vaporizer device can include a heating chamber (for example, an oven or other region in which material is heated by a heating element) configured to receive a vaporizable material directly into the heating chamber, and/or a reservoir or the like for containing the vaporizable material. In some implementations, a vaporizer device can be configured for use with a liquid vaporizable material (for example, a carrier solution in which an active and/or inactive ingredient(s) are suspended or held in solution, or a liquid form of the vaporizable material itself), a paste, a wax, and/or a solid vaporizable material. A solid vaporizable material can include a plant material that emits some part of the plant material as the vaporizable material (for example, some part of the plant material remains as waste after the material is vaporized for inhalation by a user) or optionally can be a solid form of the vaporizable material itself, such that all of the solid material can eventually be vaporized for inhalation. A liquid vaporizable material can likewise be capable of being completely vaporized, or can include some portion of the liquid material that remains after all of the material suitable for inhalation has been vaporized.

The vaporizer device can include a power supply such as, for example, a rechargeable battery. In some instances, the rechargeable battery may require rapid charging so that the user may resume use of the vaporizer device. The vaporizer device may be recharged in different manners by being connected to a variety of different external power supplies including, for example, a wired connection to an electrical outlet or a charging device (e.g., a power bank, a portable charging case, a charging adapter for an electrical outlet, and/or the like). Recharging the vaporizer device may require a different voltage, current, and/or power than the voltage, current, and/or power available from the external power supply. For example, when the vaporizer device is being charged by the charging device, the charging device may adjust the voltage, current, and/or power of the power supply (e.g., battery and/or the like) at the charging device. As will be described in greater detail below, a charging device consistent with implementations of the current subject matter may be configured to provide an efficient and effective way to charge the vaporizer device.

As noted, the vaporizer device may be charged by being coupled with charging device including, for example, a power bank, a portable charging case, a charging adapter for an electrical outlet, and/or the like. In those circumstances, the power source, for example, a battery, included in the charging device may serve as an external power supply. Charging the battery in the vaporizer device may require the presence of a voltage differential between the average voltage of the battery and the input voltage from the charging device. However, an excessively large difference between the average voltage of the battery and the input voltage from the charging device may be electrically inefficient. For example, energy may be lost when the output voltage of the charging device is increased in excess of what is required to charge the vaporizer device. Energy may also be lost when the excess voltage is dissipated as heat at the vaporizer device. Moreover, excess heat at the vaporizer device may compromise user experience.

For example, a charging device that is typically used to charge the vaporizer device may include a boost converter configured to increase the voltage of the battery at the charging device to output, for example, a 5-volt direct current. Meanwhile, the vaporizer device may include a linear charger to charge the battery in the vaporizer device. While the input to the linear charger at the vaporizer device may be the 5-volt direct current output by the charging device, the actual voltage required by the battery in the vaporizer device is typically lower. For instance, the 5-volt direct current output from the charging device may charge the battery from 3.0 volts to approximately 4.2 volts to 4.45 volts. As such, energy may be wasted in order to increase the voltage of the battery at the charging device beyond what is necessary to charge the battery at the vaporizer device. Furthermore, additional energy may be wasted when the excess input voltage is dissipated as heat at the vaporizer device.

Accordingly, in some implementations of the current subject matter, a charging device may include a voltage controller configured to regulate, while the vaporizer device is being charged with the charging device, the output voltage of the charging device based on the voltage of the battery in the vaporizer device. The voltage controller may provide a closed-loop control of the output voltage of the charging device such that the output voltage of the charging device is maintained at a threshold voltage above the voltage of the battery in the vaporizer device. Eliminating an excess voltage differential between the output voltage of the charging device and the voltage of the battery during the charging of the vaporizer device may increase electrical efficiency as well as minimize the heat that is generated as a result of the charging process. A charging device having one or more features consistent with various implementations of the current subject matter may therefore provide advantages and improvements relative to existing approaches, while also introducing additional benefits as described herein. Moreover, it should be appreciated that a charging device having one or more features consistent with various implementations of the current subject matter may be used to charge a variety of electronic devices including vaporizer devices.

A vaporizer device consistent with implementations of the current subject matter may be configured to couple with a vaporizer cartridge including a vaporizable material. That is, the vaporizable material may be contained in a reservoir included in the vaporizer cartridge that can be coupled (and decoupled) from the vaporizer device. Moreover, the vaporizer cartridge may be refillable when empty, or disposable such that a new cartridge containing additional vaporizable material of a same or different type can be used). Nevertheless, it should be appreciated that a power controller consistent with various implementations of the current subject matter may be compatible with any type of vaporizer device including, for example, a cartridge-based vaporizer device, a cartridge-less vaporizer device, a multi-use vaporizer device capable of use with or without a cartridge, and/or the like.

In some implementations of the current subject matter, the vaporizer device can include a heating chamber (for example, an oven or other region in which material is heated by a heating element) configured to receive a vaporizable material directly into the heating chamber, and/or a reservoir or the like for containing the vaporizable material. The vaporizer device can be configured for use with a liquid vaporizable material (for example, a carrier solution in which an active and/or inactive ingredient(s) are suspended or held in solution, or a liquid form of the vaporizable material itself), a paste, a wax, and/or a solid vaporizable material. A solid vaporizable material can include a plant material that emits some part of the plant material as the vaporizable material (for example, some part of the plant material remains as waste after the material is vaporized for inhalation by a user) or optionally can be a solid form of the vaporizable material itself, such that all of the solid material can eventually be vaporized for inhalation. A liquid vaporizable material can likewise be capable of being completely vaporized, or can include some portion of the liquid material that remains after all of the material suitable for inhalation has been vaporized.

To further illustrate, FIG. 1A depicts a block diagram illustrating an example of a vaporizer device 100 consistent with implementations of the current subject matter. Referring to FIG. 1A, the vaporizer device 100 can include a power source 112 (for example, a battery, which can be a rechargeable battery), and a controller 104 (for example, a processor, circuitry, etc. capable of executing logic) for controlling delivery of heat to an atomizer 141 to cause a vaporizable material 102 to be converted from a condensed form (such as a solid, a liquid, a solution, a suspension, a part of an at least partially unprocessed plant material, etc.) to the gas phase. The controller 104 can be part of one or more printed circuit boards (PCBs) consistent with certain implementations of the current subject matter. After conversion of the vaporizable material 102 to the gas phase, at least some of the vaporizable material 102 in the gas phase can condense to form particulate matter in at least a partial local equilibrium with the gas phase as part of an aerosol, which can form some or all of an inhalable dose provided by the vaporizer device 100 during a user's puff or draw on the vaporizer device 100. It should be appreciated that the interplay between gas and condensed phases in an aerosol generated by a vaporizer device 100 can be complex and dynamic, due to factors such as ambient temperature, relative humidity, chemistry, flow conditions in airflow paths (both inside the vaporizer and in the airways of a human or other animal), and/or mixing of the vaporizable material 102 in the gas phase or in the aerosol phase with other air streams, which can affect one or more physical parameters of an aerosol. In some vaporizer devices, and particularly for vaporizer devices configured for delivery of volatile vaporizable materials, the inhalable dose can exist predominantly in the gas phase (for example, formation of condensed phase particles can be very limited).

The atomizer 141 in the vaporizer device 100 can be configured to vaporize a vaporizable material 102. The vaporizable material 102 can be a liquid. Examples of the vaporizable material 102 include neat liquids, suspensions, solutions, mixtures, and/or the like. The atomizer 141 can include a wicking element (e.g., a wick) configured to convey an amount of the vaporizable material 102 to a part of the atomizer 141 that includes a heating element (not shown in FIG. 1A).

For example, the wicking element can be configured to draw the vaporizable material 102 from a reservoir 140 configured to contain the vaporizable material 102, such that the vaporizable material 102 can be vaporized by heat delivered from a heating element. The wicking element can also optionally allow air to enter the reservoir 140 and replace the volume of vaporizable material 102 removed. In some implementations of the current subject matter, capillary action can pull vaporizable material 102 into the wick for vaporization by the heating element, and air can return to the reservoir 140 through the wick to at least partially equalize pressure in the reservoir 140. Other methods of allowing air back into the reservoir 140 to equalize pressure are also within the scope of the current subject matter.

As used herein, the terms "wick" or "wicking element" include any material capable of causing fluid motion via capillary pressure.

The heating element can include one or more of a conductive heater, a radiative heater, and/or a convective heater. One type of heating element is a resistive heating element, which can include a material (such as a metal or alloy, for example a nickel-chromium alloy, or a non-metallic resistor) configured to dissipate electrical power in the form of heat when electrical current is passed through one or more resistive segments of the heating element. In some implementations of the current subject matter, the atomizer 141 can include a heating element which includes a resistive coil or other heating element wrapped around, positioned within, integrated into a bulk shape of, pressed into thermal contact with, or otherwise arranged to deliver heat to a wicking element, to cause the vaporizable material 102 drawn from the reservoir 140 by the wicking element to be vaporized for subsequent inhalation by a user in a gas and/or a condensed (for example, aerosol particles or droplets) phase. Other wicking elements, heating elements, and/or atomizer configurations are also possible.

Certain vaporizer devices may, additionally or alternatively, be configured to create an inhalable dose of the vaporizable material 102 in the gas phase and/or aerosol phase via heating of the vaporizable material 102. The vaporizable material 102 can be a solid-phase material (such as a wax or the like) or plant material (for example, tobacco leaves and/or parts of tobacco leaves). In such vaporizer devices, a resistive heating element can be part of, or otherwise incorporated into or in thermal contact with, the walls of an oven or other heating chamber into which the vaporizable material 102 is placed. Alternatively, a resistive heating element or elements can be used to heat air passing through or past the vaporizable material 102, to cause convective heating of the vaporizable material 102. In still other examples, a resistive heating element or elements can be disposed in intimate contact with plant material such that direct conductive heating of the plant material occurs from within a mass of the plant material, as opposed to only by conduction inward from walls of an oven.

The heating element can be activated in association with a user puffing (e.g., drawing, inhaling, etc.) on a mouthpiece 130 of the vaporizer device 100 to cause air to flow from an air inlet, along an airflow path that passes the atomizer 141 (e.g., wicking element and heating element). Optionally, air can flow from an air inlet through one or more condensation areas or chambers, to an air outlet in the mouthpiece 130. Incoming air moving along the airflow path moves over or through the atomizer 141, where vaporizable material 102 in the gas phase is entrained into the air. The heating element can be activated via the controller 104, which can optionally be a part of a vaporizer body 110 as discussed herein, causing current to pass from the power source 112 through a circuit including the resistive heating element, which is optionally part of a vaporizer cartridge 120 as discussed herein. As noted herein, the entrained vaporizable material 102 in the gas phase can condense as it passes through the remainder of the airflow path such that an inhalable dose of the vaporizable material 102 in an aerosol form can be delivered from the air outlet (for example, the mouthpiece 130) for inhalation by a user.

Activation of the heating element can be caused by automatic detection of a puff based on one or more signals generated by one or more sensor(s) 113. The sensor 113 and the signals generated by the sensor 113 can include one or more of: a pressure sensor or sensors disposed to detect pressure along the airflow path relative to ambient pressure (or optionally to measure changes in absolute pressure), a motion sensor or sensors (for example, an accelerometer) of the vaporizer device 100, a flow sensor or sensors of the vaporizer device 100, a capacitive lip sensor of the vaporizer device 100, detection of interaction of a user with the vaporizer device 100 via one or more input devices 116 (for example, buttons or other tactile control devices of the vaporizer device 100), receipt of signals from a computing device in communication with the vaporizer device 100, and/or via other approaches for determining that a puff is occurring or imminent.

As discussed herein, the vaporizer device 100 consistent with implementations of the current subject matter can be configured to connect (such as, for example, wirelessly or via a wired connection) to a computing device (or optionally two or more devices) in communication with the vaporizer device 100. To this end, the controller 104 can include communication hardware 105. The controller 104 can also include a memory 108. The communication hardware 105 can include firmware and/or can be controlled by software for executing one or more cryptographic protocols for the communication.

A computing device can be a component of a vaporizer system that also includes the vaporizer device 100, and can include its own hardware for communication, which can establish a wireless communication channel with the communication hardware 105 of the vaporizer device 100. For example, a computing device used as part of a vaporizer system can include a general-purpose computing device (such as a smartphone, a tablet, a personal computer, some other portable device such as a smartwatch, or the like) that executes software to produce a user interface for enabling a user to interact with the vaporizer device 100. In other implementations of the current subject matter, such a device used as part of a vaporizer system can be a dedicated piece of hardware such as a remote control or other wireless or wired device having one or more physical or soft (e.g., configurable on a screen or other display device and select-able via user interaction with a touch-sensitive screen or some other input device like a mouse, pointer, trackball, cursor buttons, or the like) interface controls. The vaporizer device 100 can also include one or more outputs 117 or devices for providing information to the user. For example, the outputs 117 can include one or more light emitting diodes (LEDs) configured to provide feedback to a user based on a status and/or mode of operation of the vaporizer device 100.

In the example in which a computing device provides signals related to activation of the resistive heating element, or in other examples of coupling of a computing device with the vaporizer device 100 for implementation of various control or other functions, the computing device executes one or more computer instruction sets to provide a user interface and underlying data handling. In one example, detection by the computing device of user interaction with one or more user interface elements can cause the computing device to signal the vaporizer device 100 to activate the heating element to reach an operating temperature for creation of an inhalable dose of vapor/aerosol. Other functions of the vaporizer device 100 can be controlled by interaction of a user with a user interface on a computing device in communication with the vaporizer device 100.

The temperature of a resistive heating element of the vaporizer device 100 can depend on a number of factors, including an amount of electrical power delivered to the resistive heating element and/or a duty cycle at which the electrical power is delivered, conductive heat transfer to other parts of the vaporizer device 100 and/or to the environment, latent heat losses due to vaporization of the vaporizable material 102 from the wicking element and/or the atomizer 141 as a whole, and convective heat losses due to airflow (e.g., air moving across the heating element or the atomizer 141 as a whole when a user inhales on the vaporizer device 100). As noted herein, to reliably activate the heating element or heat the heating element to a desired temperature, the vaporizer device 100 may, in some implementations of the current subject matter, make use of signals from the sensor 113 (for example, a pressure sensor) to determine when a user is inhaling. The sensor 113 can be positioned in the airflow path and/or can be connected (for example, by a passageway or other path) to an airflow path containing an inlet for air to enter the vaporizer device 100 and an outlet via which the user inhales the resulting vapor and/or aerosol such that the sensor 113 experiences changes (for example, pressure changes) concurrently with air passing through the vaporizer device 100 from the air inlet to the air outlet. In some implementations of the current subject matter, the heating element can be activated in association with a user's puff, for example by automatic detection of the puff, or by the sensor 113 detecting a change (such as a pressure change) in the airflow path.

The sensor 113 can be positioned on or coupled to (e.g., electrically or electronically connected, either physically or via a wireless connection) the controller 104 (for example, a printed circuit board or other type of circuit board). To take measurements accurately and maintain durability of the vaporizer device 100, it can be beneficial to provide a seal 127 resilient enough to separate an airflow path from other parts of the vaporizer device 100. The seal 127, which can be a gasket, can be configured to at least partially surround the sensor 113 such that connections of the sensor 113 to the internal circuitry of the vaporizer device 100 are separated from a part of the sensor 113 exposed to the airflow path. In an example of a cartridge-based vaporizer, the seal 127 can also separate parts of one or more electrical connections between the vaporizer body 110 and the vaporizer cartridge 120. Such arrangements of the seal 127 in the vaporizer device 100 can be helpful in mitigating against potentially disruptive impacts on vaporizer components resulting from interactions with environmental factors such as water in the vapor or liquid phases, other fluids such as the vaporizable material 102, etc., and/or to reduce the escape of air from the designated airflow path in the vaporizer device 100. Unwanted air, liquid or other fluid passing and/or contacting circuitry of the vaporizer device 100 can cause various unwanted effects, such as altered pressure readings, and/or can result in the buildup of unwanted material, such as moisture, excess vaporizable material 102, etc., in parts of the vaporizer device 100 where they can result in poor pressure signal, degradation of the sensor 113 or other components, and/or a shorter life of the vaporizer device 100. Leaks in the seal 127 can also result in a user inhaling air that has passed over parts of the vaporizer device 100 containing, or constructed of, materials that may not be desirable to be inhaled.

In some implementations, the vaporizer body 110 includes the controller 104, the power source 112 (for example, a battery), one more of the sensor 113, charging contacts (such as those for charging the power source 112), the seal 127, and a cartridge receptacle 118 configured to receive the vaporizer cartridge 120 for coupling with the vaporizer body 110 through one or more of a variety of attachment structures. In some examples, the vaporizer cartridge 120 includes the reservoir 140 for containing the vaporizable material 102, and the mouthpiece 130 has an aerosol outlet for delivering an inhalable dose to a user. The vaporizer cartridge 120 can include the atomizer 141 having a wicking element and a heating element. Alternatively, one or both of the wicking element and the heating element can be part of the vaporizer body 110. In implementations in which any part of the atomizer 141 (e.g., heating element and/or wicking element) is part of the vaporizer body 110, the vaporizer device 100 can be configured to supply vaporizable material 102 from the reservoir 140 in the vaporizer cartridge 120 to the part(s) of the atomizer 141 included in the vaporizer body 110.

Cartridge-based configurations for the vaporizer device 100 that generate an inhalable dose of a vaporizable material 102 that is not a liquid, via heating of a non-liquid material, are also within the scope of the current subject matter. For example, the vaporizer cartridge 120 can include a mass of a plant material that is processed and formed to have direct contact with parts of one or more resistive heating elements, and the vaporizer cartridge 120 can be configured to be coupled mechanically and/or electrically to the vaporizer body 110 that includes the controller 104, the power source 112, and one or more receptacle contacts 125a and 125b configured to connect to one or more corresponding cartridge contacts 124a and 125b and complete a circuit with the one or more resistive heating elements.

In an embodiment of the vaporizer device 100 in which the power source 112 is part of the vaporizer body 110, and a heating element is disposed in the vaporizer cartridge 120 and configured to couple with the vaporizer body 110, the vaporizer device 100 can include electrical connection features (for example, means for completing a circuit) for completing a circuit that includes the controller 104 (for example, a printed circuit board, a microcontroller, or the like), the power source 112, and the heating element (for example, a heating element within the atomizer 141). These features can include one or more contacts (referred to herein as cartridge contacts 124a and 124b) on a bottom surface of the vaporizer cartridge 120 and at least two contacts (referred to herein as receptacle contacts 125a and 125b) disposed near a base of the cartridge receptacle 118 of the vaporizer device 100 such that the cartridge contacts 124a and 124b and the receptacle contacts 125a and 125b make electrical connections when the vaporizer cartridge 120 is inserted into and coupled with the cartridge receptacle 118. The circuit completed by these electrical connections can allow delivery of electrical current to a heating element and can further be used for additional functions, such as measuring a resistance of the heating element for use in determining and/or controlling a temperature of the heating element based on a thermal coefficient of resistivity of the heating element.

In some implementations of the current subject matter, the cartridge contacts 124a and 124b and the receptacle contacts 125a and 125b can be configured to electrically connect in either of at least two orientations. In other words, one or more circuits necessary for operation of the vaporizer device 100 can be completed by insertion of the vaporizer cartridge 120 into the cartridge receptacle 118 in a first rotational orientation (around an axis along which the vaporizer cartridge 120 is inserted into the cartridge receptacle 118 of the vaporizer body 110) such that the cartridge contact 124a is electrically connected to the receptacle contact 125a and the cartridge contact 124b is electrically connected to the receptacle contact 125b. Furthermore, the one or more circuits necessary for operation of the vaporizer device 100 can be completed by insertion of the vaporizer cartridge 120 in the cartridge receptacle 118 in a second rotational orientation such cartridge contact 124a is electrically connected to the receptacle contact 125b and cartridge contact 124b is electrically connected to the receptacle contact 125a.

In one example of an attachment structure for coupling the vaporizer cartridge 120 to the vaporizer body 110, the vaporizer body 110 includes one or more detents (for example, dimples, protrusions, etc.) protruding inwardly from an inner surface of the cartridge receptacle 118, additional material (such as metal, plastic, etc.) formed to include a portion protruding into the cartridge receptacle 118, and/or the like. One or more exterior surfaces of the vaporizer cartridge 120 can include corresponding recesses (not shown in FIG. 1A) that can fit and/or otherwise snap over such detents or protruding portions when the vaporizer cartridge 120 is inserted into the cartridge receptacle 118 on the vaporizer body 110. When the vaporizer cartridge 120 and the vaporizer body 110 are coupled (e.g., by insertion of the vaporizer cartridge 120 into the cartridge receptacle 118 of the vaporizer body 110), the detents or protrusions of the vaporizer body 110 can fit within and/or otherwise be held within the recesses of the vaporizer cartridge 120, to hold the vaporizer cartridge 120 in place when assembled. Such can provide enough support to hold the vaporizer cartridge 120 in place to ensure good contact between the cartridge contacts 124a and 124b and the receptacle contacts 125a and 125b, while allowing release of the vaporizer cartridge 120 from the vaporizer body 110 when a user pulls with reasonable force on the vaporizer cartridge 120 to disengage the vaporizer cartridge 120 from the cartridge receptacle 118.

In some implementations, the vaporizer cartridge 120, or at least an insertable end 122 of the vaporizer cartridge 120 configured for insertion in the cartridge receptacle 118, can have a non-circular cross section transverse to the axis along which the vaporizer cartridge 120 is inserted into the cartridge receptacle 118. For example, the non-circular cross section can be approximately rectangular, approximately elliptical (e.g., have an approximately oval shape), non-rectangular but with two sets of parallel or approximately parallel opposing sides (e.g., having a parallelogram-like shape), or other shapes having rotational symmetry of at least order two. In this context, approximate shape indicates that a basic likeness to the described shape is apparent, but that sides of the shape in question need not be completely linear and vertices need not be completely sharp. Rounding of both or either of the edges or the vertices of the cross-sectional shape is contemplated in the description of any non-circular cross section referred to herein.

The cartridge contacts 124a and 124b and the receptacle contacts 125a and 125b can take various forms. For example, one or both sets of contacts can include conductive pins, tabs, posts, receiving holes for pins or posts, or the like. Some types of contacts can include springs or other features to facilitate better physical and electrical contact between the contacts on the vaporizer cartridge 120 and the vaporizer body 110. The electrical contacts can optionally be gold-plated, and/or include other materials.

Figure 1B:
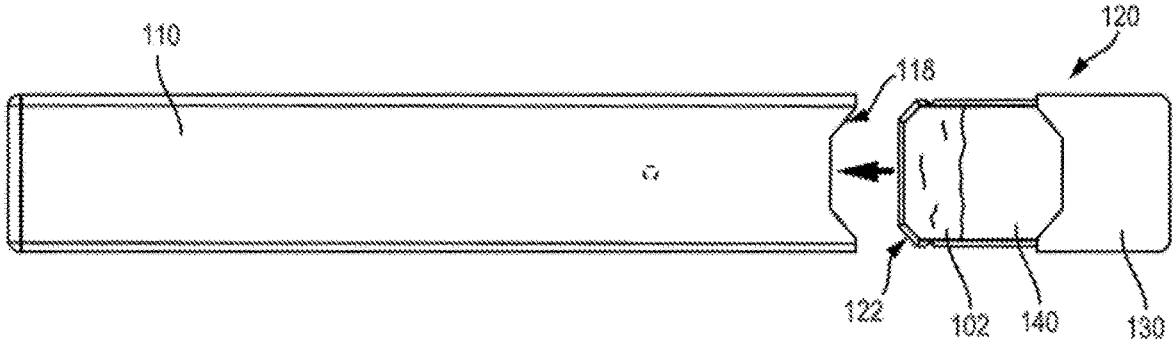
FIG. 1B depicts a top view of an example of a vaporizer device and a vaporizer cartridge consistent with implementations of the current subject matter.
Figure 1C:
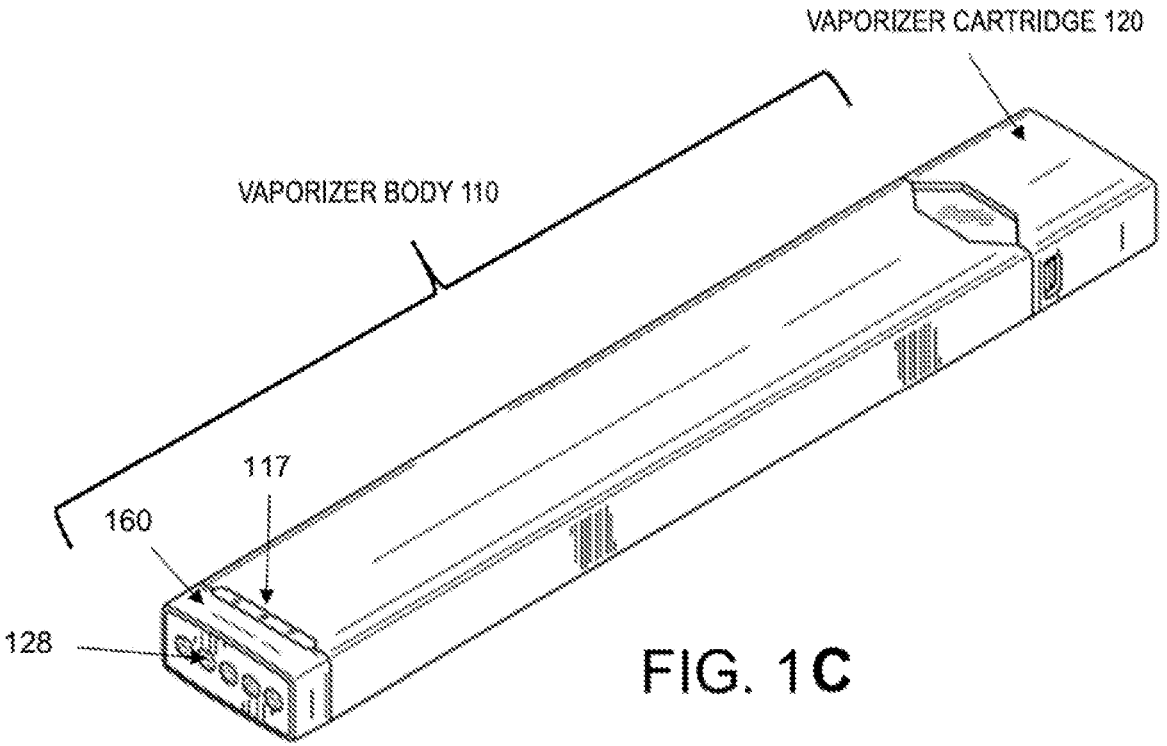
FIG. 1C depicts a perspective view of an example of a vaporizer cartridge coupled to a vaporizer device consistent with implementations of the current subject matter.

FIG. 1B depicts a top view of an example of the vaporizer device 100 and the vaporizer cartridge 120 consistent with implementations of the current subject matter. As shown in FIG. 1B, of the vaporizer cartridge 120 may be releasably inserted into the cartridge receptacle 118 of the vaporizer body 110. In the example shown in FIG. 1B, the vaporizer cartridge 120 is positioned for insertion into the vaporizer body 110. Meanwhile, FIG. 1C depicts a perspective view of the vaporizer device 100 having the vaporizer cartridge 120 inserted (e.g., releasably) into the cartridge receptacle 118 of the vaporizer body 110. When a user puffs on the vaporizer device 100, air can pass between an outer surface of the vaporizer cartridge 120 and an inner surface of the cartridge receptacle 118 on the vaporizer body 110. Air can then be drawn into the insertable end 122 of the cartridge, through the vaporization chamber that includes or contains the heating element and wick, and out through an outlet of the mouthpiece 130 for delivery of the inhalable aerosol to a user. The reservoir 140 of the vaporizer cartridge 120 can be formed in whole or in part from translucent material such that a level of the vaporizable material 102 is visible within the vaporizer cartridge 120. The mouthpiece 130 can be a separable component of the vaporizer cartridge 120 or can be integrally formed with other component(s) of the vaporizer cartridge 120 (for example, formed as a unitary structure with the reservoir 140 and/or the like).

Further to the discussion above regarding the electrical connections between the vaporizer cartridge 120 and the vaporizer body 110 being reversible such that at least two rotational orientations of the vaporizer cartridge 120 in the cartridge receptacle 118 are possible, in some embodiments of the vaporizer device 100, the shape of the vaporizer cartridge 120, or at least a shape of the insertable end 122 of the vaporizer cartridge 120 that is configured for insertion into the cartridge receptacle 118, can have rotational symmetry of at least order two. In other words, the vaporizer cartridge 120 or at least the insertable end 122 of the vaporizer cartridge 120 can be symmetrical upon a rotation of 180° around an axis along which the vaporizer cartridge 120 is inserted into the cartridge receptacle 118. In such a configuration, the circuitry of the vaporizer device 100 can support identical operation regardless of which symmetrical orientation of the vaporizer cartridge 120 occurs.

Referring again to FIG. 1C, the vaporizer device 100 can include one or more output features 117 configured to provide a visual indicator, an audio indicator, and/or a haptic indicator of a status, mode of operation, and/or the like, of the vaporizer device 100. In some aspects, the one or more output features 117 can include a plurality of LEDs (e.g., two, three, four, five, or six LEDs). The one or more output feature 117 (e.g., each individual LED) can be configured to display light in one or more colors (for example, white, red, blue, green, yellow, etc.). Alternatively and/or additionally, the one or more output features 117 can be configured to display different light patterns (for example, by illuminating specific LEDs, varying a light intensity of one or more of the LEDs over time, illuminating one or more LEDs with a different color, and/or the like) corresponding to different statuses, modes of operation, and/or the like of the vaporizer device 100. In the example shown in FIG. 1C, the one or more output features 117 can be proximal to and/or at least partially disposed within a bottom end region 160 of the vaporizer device 100. Further as shown in FIG. 1C, the vaporizer device 100 may, additionally or alternatively, include one or more externally accessible charging contacts 128, which can be proximate to and/or at least partially disposed within the bottom end region 160 of the vaporizer device 100.

Figure 1D:
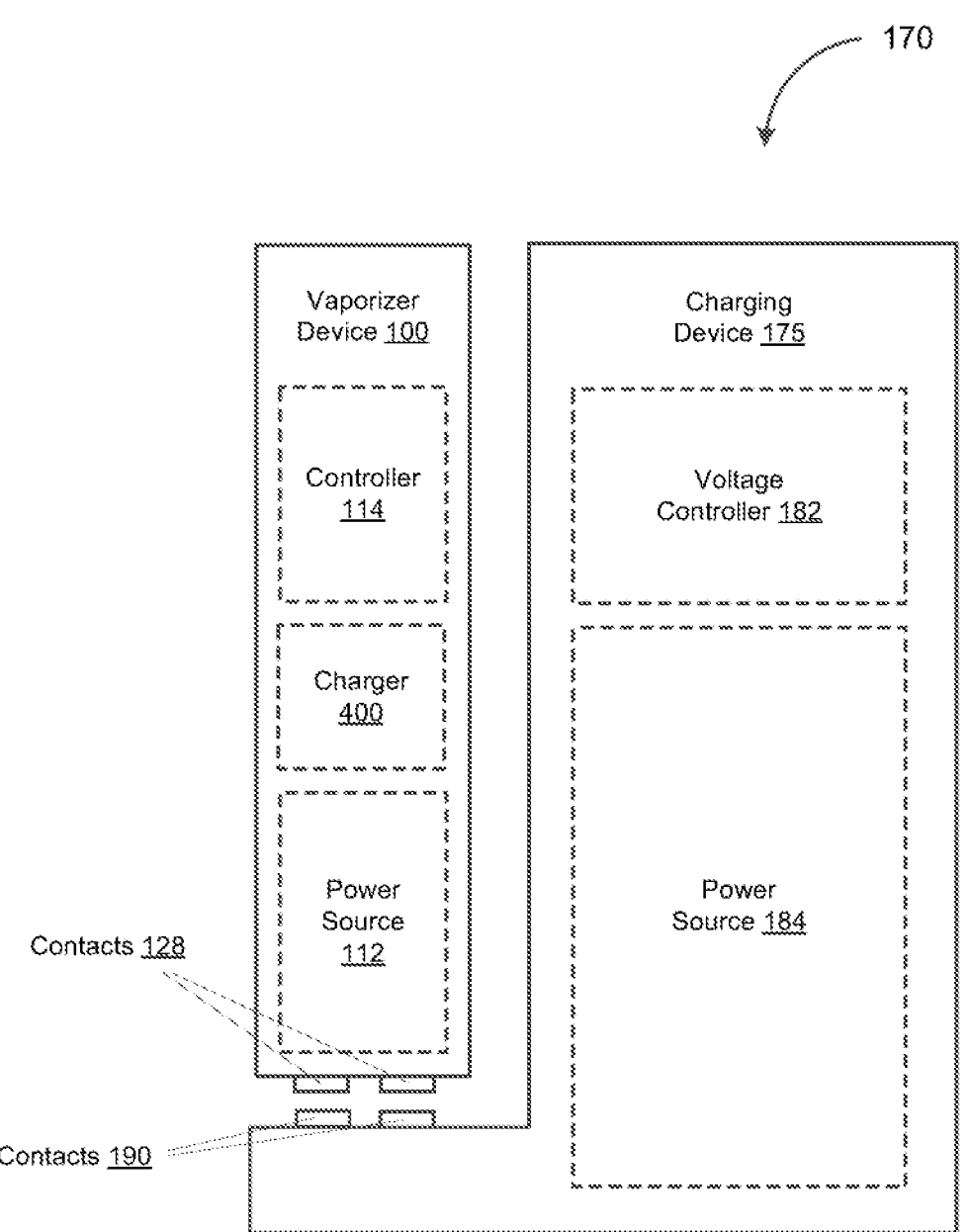
FIG. 1D depicts a block diagram illustrating an example of a charging system including a vaporizer device and a charging device consistent with implementations of the current subject matter.

FIG. 1D depicts a block diagram illustrating an example of a charging system 170 including the vaporizer device 100 and a charging device 175 consistent with implementations of the current subject matter. Referring to FIGS. 1A-D, the vaporizer device 100 may be charged by being coupled with the charging device 175, which may be, for example, a power bank, a portable charging case, a charging adapter for an electrical outlet, and/or the like. For example, as shown in FIG. 1D, an electric coupling may be formed between the vaporizer device 100 and the charging device 175 when one or more contacts 128 at the vaporizer device 100 are coupled with one or more contacts 190 at the charging device 175. Although FIG. 1D shows the charging device 175 charging the vaporizer device 100, it should be appreciated that the charging device 175 may also be configured to charge a different type of electronic device.

As shown in FIG. 1D, the charging device 175 may include a voltage controller 182 and a power source 184. When coupled with the vaporizer device 100, the power source 184 may serve as an external power supply for charging the power source 112 in the vaporizer device 100. The power source 184 may include one or more battery cells included in the charging device 175. Alternatively, where the charging device 175 may be a charging adapter, the power source 184 may be an electrical outlet connected to an electrical grid.

The charging device 175 may be configured to provide, to the vaporizer device 100, a charging current configured to charge the power source 112 at the vaporizer device 100. In some implementations of the current subject matter, the voltage controller 182 may be configured to regulate the output voltage of the charging device 175 while the vaporizer device 100 is being charged by the charging device 175. The voltage controller 182 may regulate the output voltage of the charging device 175 such that the output voltage of the charging device 175 is adequate for charging the vaporizer device 100. For example, the voltage controller 182 may regulate the output voltage of the charging device 175 such that the output voltage of the charging device 175 is a threshold voltage above a voltage of the power source 112 at the vaporizer device 100. Moreover, the voltage controller 182 may regulate the output voltage of the charging device 175 such that the output voltage of the charging device 175 is not in excess of the voltage required to charge the vaporizer device 100. For instance, the voltage controller 182 may be configured to maintain a predetermined voltage differential between the output voltage of the charging device 175 and the voltage of the power source 112 at the vaporizer device 100. In some implementations, the voltage controller 182 regulates the output voltage of the charging device 175 by boosting (e.g., via a boost converter) a voltage of the power source 184 in order to increase the voltage to a voltage that is capable of efficiently charge the vaporizer device 100.

In some implementations of the current subject matter, the voltage controller 182 may be communicatively coupled with the controller 104 at the vaporizer device 100 such that the voltage controller 182 may receive, from the controller 104, one or more indications of a current voltage of the power source 112 at the vaporizer device 100. Alternatively, the voltage controller 182 may receive, from the controller 104 at the vaporizer device 100, one or more indications of a desired voltage requested by the vaporizer device 100 in order to charge the power source 112. The desired voltage requested by the vaporizer device 100 may be threshold voltage above the current voltage of the power source 112.

The voltage controller 182 may adjust, based at least on the indications received from the vaporizer device 100, the output voltage of the charging device 175 such that the output voltage of the charging device 175 is no more than the threshold voltage above the current voltage of the power source 112 at the vaporizer device 100. That is, the output voltage of the charging device 175 may be adjusted to maintain a predetermined voltage differential between the output voltage of the charging device 175 and the current voltage of the power source 112. By avoiding an excessive voltage differential between the output voltage of the charging device 175 and the current voltage of the power source 112, the voltage controller 182 may increase the electrical efficiency of the charging process. For example, the voltage controller 182 may reduce (or eliminate) a level of boost level applied to a voltage received from the power source 184 (e.g., via a boost converter included in the voltage controller 182) prior to outputting power from the charging device 175 to the vaporizer device 100. Moreover, the voltage controller 182 may avoid outputting an excess voltage to the vaporizer device 100, which would be dissipated as heat at the vaporizer device 100 and which could compromise the user experience associated with the vaporizer device 100.

In some implementations of the current subject matter, the vaporizer device 100 may couple to the charging device 175 via one or more charging adapters. FIGS. 2A-F depict one example of a charging adapter 250 consistent with implementations of the current subject matter. For example, FIG.

Figure 2A:
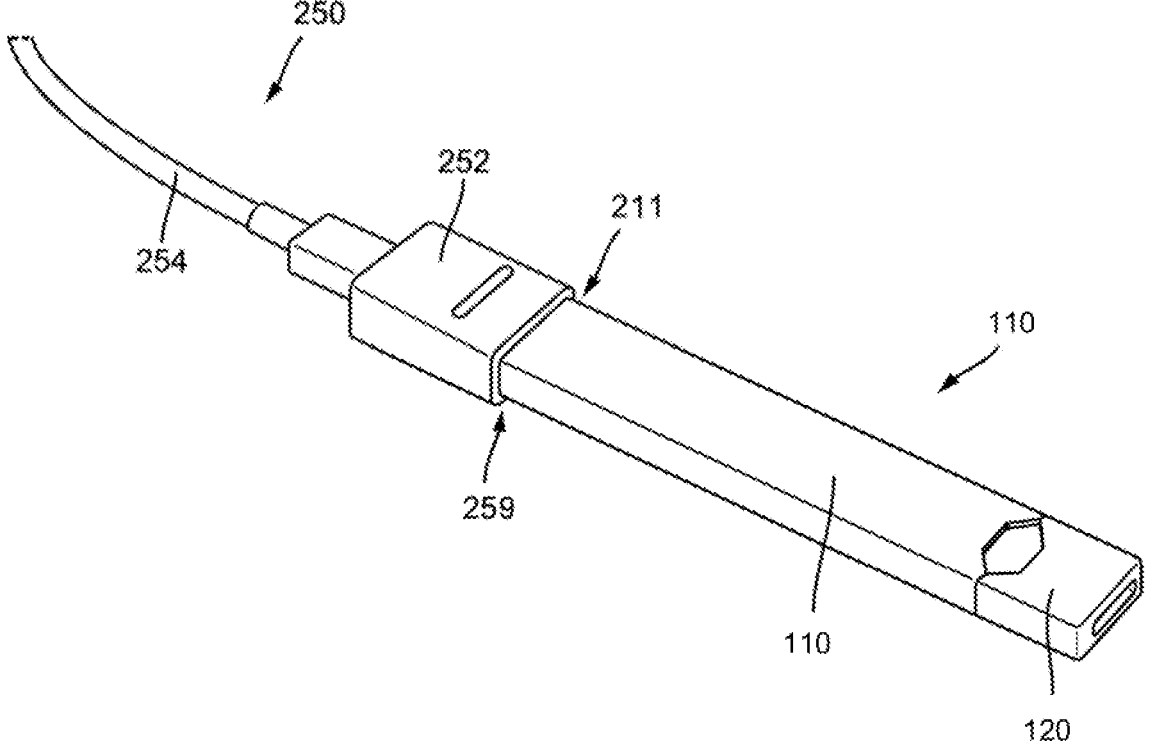
FIG. 2A depicts a top perspective view of an example of a vaporizer device coupled to a charging adapter consistent with implementations of the current subject matter.

2A illustrates the vaporizer device 100 being coupled with the charging adapter 250, which may be further coupled to the charging device 175 in order for the vaporizer device 100 to be charged by the charging device 175. As shown in FIG. 2A, the charging adapter 250 can include a charging body 252 with a cable 254 extending therefrom for connecting to an external power source (e.g., via a plug, USB feature, etc.). A charging end 211 (including, for example, the bottom end region 160) of the vaporizer device 100, which may include one or more charging contacts (e.g., the contacts 128), may be inserted into a coupling end 259 of the charging body 252, thereby coupling the charging end 211 of the vaporizer device 100 to the charging body 252, as shown in FIG. 2A. Although shown as coupling the vaporizer body 110 of the vaporizer device 100 to the charging adapter 250, some configurations of the charging adapter 250 may be configured to accept, instead of the vaporizer body 110, at least a portion of the cartridge 120 coupled to the vaporizer body 110.

Figure 2B:
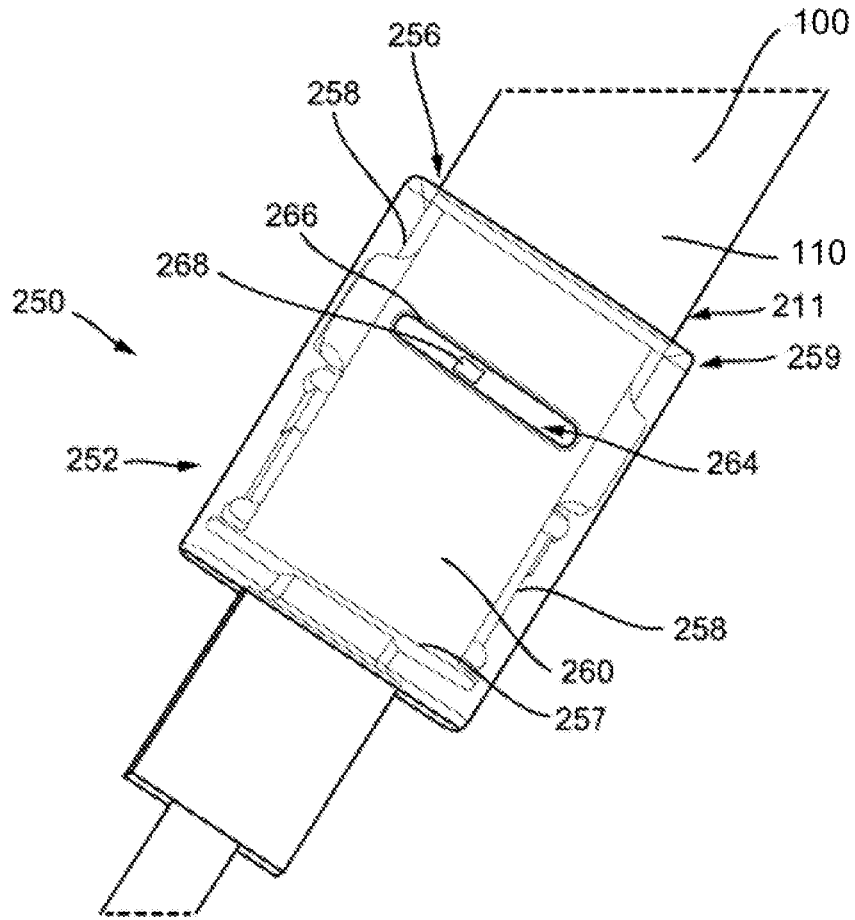
FIG. 2B depicts a top transparent view of a distal end of a charging adapter consistent with implementations of the current subject matter.
Figure 2C:
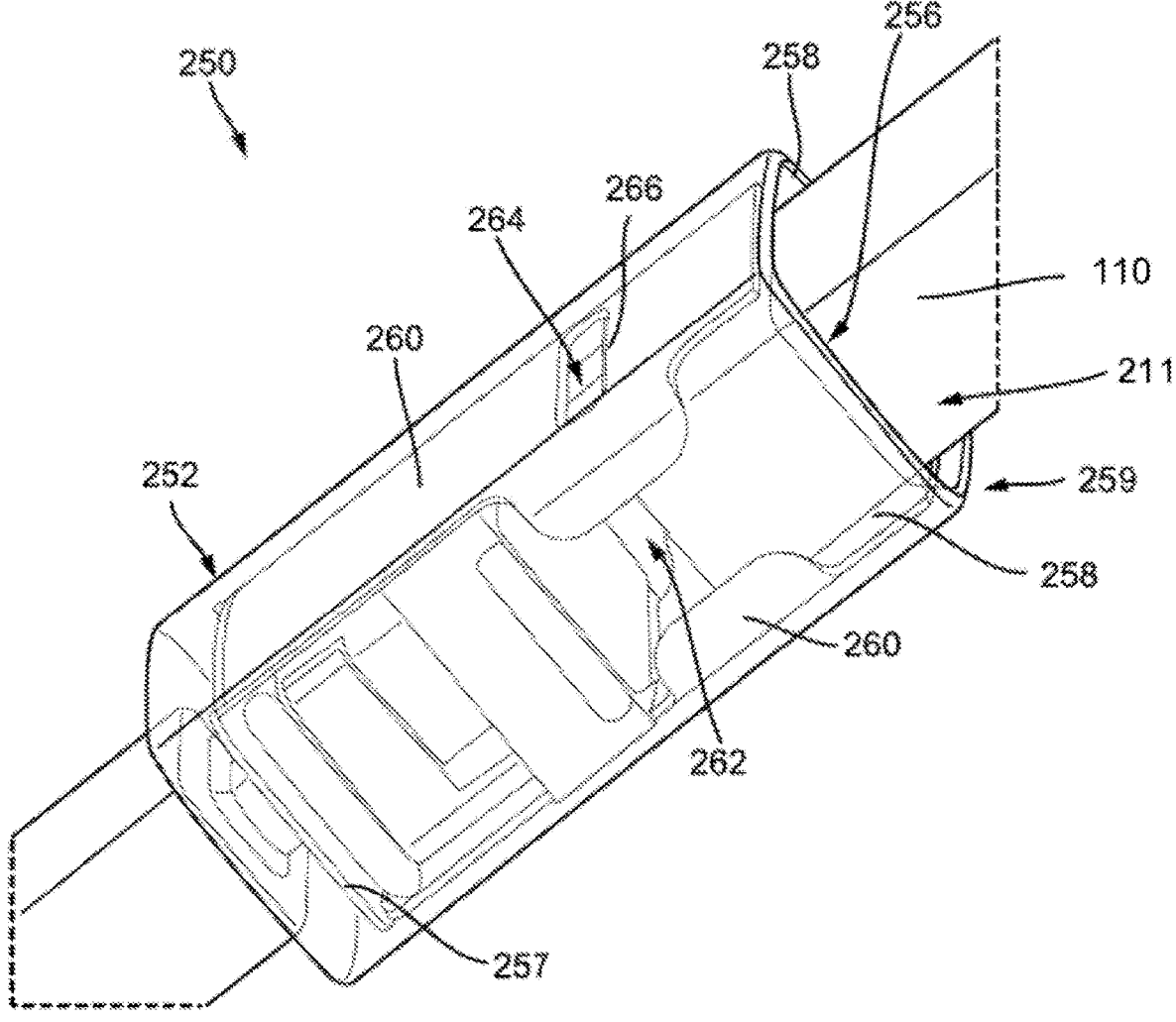
FIG. 2C depicts a side perspective transparent view of an example of a charging body consistent with implementations of the current subject matter.

Referring now to FIGS. 2B-C, the charging body 252 may include a chamber 256 defined by a bottom surface 257 and chamber walls 258 forming a perimeter of the chamber 256. For example, the chamber 256 may include a square or rectangular volume defined by four chamber walls 258 extending between the bottom surface 257 of the chamber 256 and an end surface of the coupling end 259 of the charging body 252. As shown in FIGS. 2E-F, in some embodiments, the bottom surface 257 of the chamber 256 may include one or more charging contacts 261 that may mate with the one or more charging contacts of the vaporizer device 100 (e.g., the contacts 128) in order to charge the vaporizer device 100. The chamber walls 258 may provide coupling support between the vaporizer device 100 and charging body 252, and may assist in retaining the vaporizer device 100 in the chamber 256 of the charging body 252, such as while the vaporizer device 100 is being charged via the charging adapter 250.

In some embodiments, the charging body 252 may be constructed from a material that allows at least the chamber walls 258 (or at least a portion thereof) to flex. For example, the chamber walls 258 may be formed from a pliable and/or semi-pliable material (e.g., silicon, plastic, natural rubber, and/or the like) that is capable of expanding and contracting such that the chamber 256 is capable of receiving a cleaning tool. Such cleaning of the chamber 256, which includes the charging contacts 261, may lengthen the lifespan and/or efficient and effective use of the charging adapter 250 by allowing the removal of extraneous material that may interfere with the charging of the vaporizer device 100. Other benefits associated with such features may be appreciated and are within the scope of this disclosure.

Figure 2D:
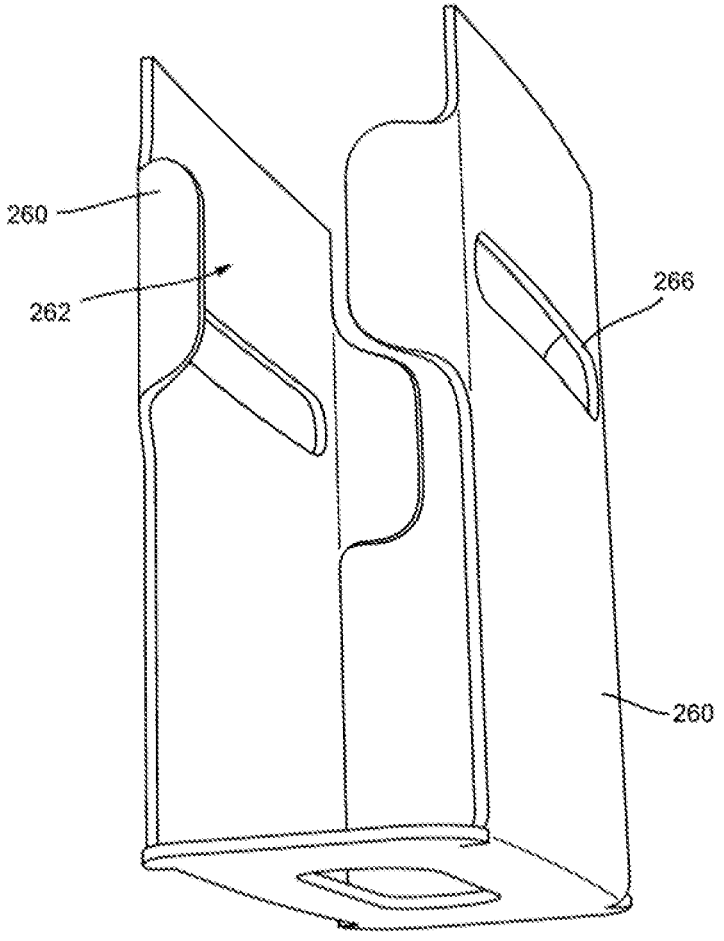
FIG. 2D depicts a side perspective view of an example of a support consistent with implementations of the current subject matter.
Figure 2E:
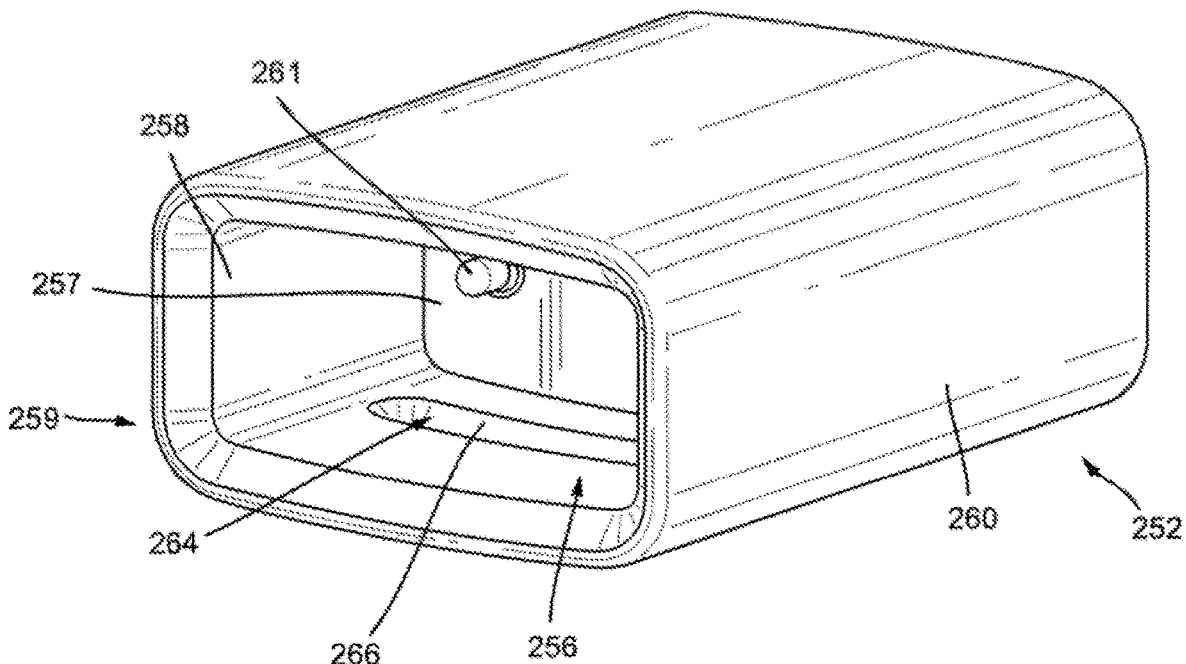
FIG. 2E depicts a side isometric view of an example of a charging body consistent with implementations of the current subject matter.
Figure 2F:
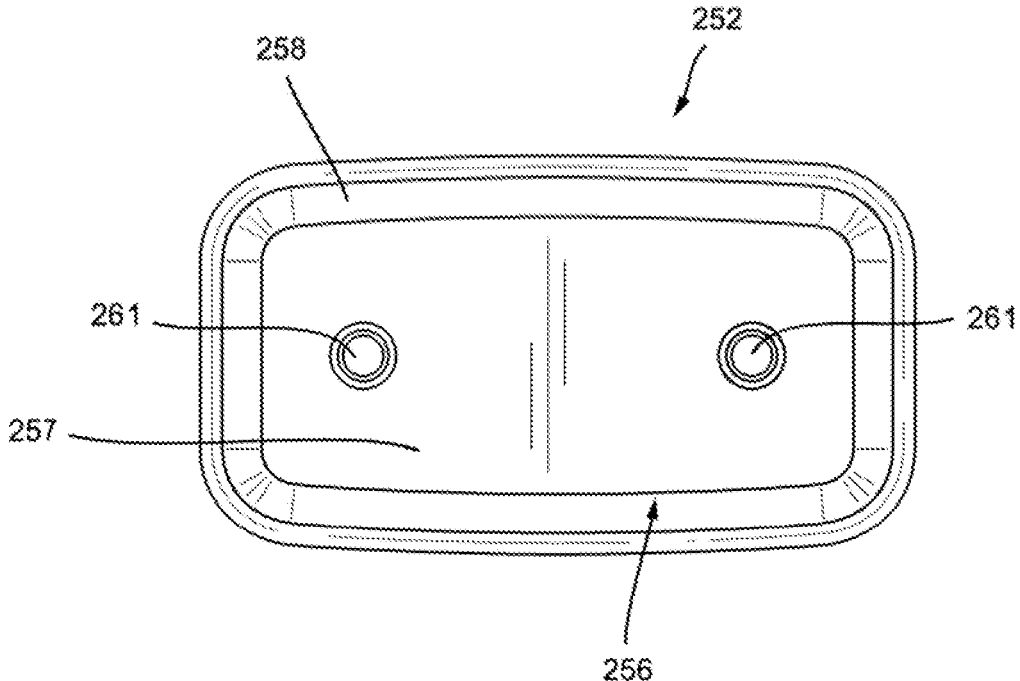
FIG. 2F depicts an end view of an example of a charging body consistent with implementations of the current subject matter.

As shown in FIGS. 2B-D, the charging body 252 may include a support 260, which may be made out of a material that is stiffer compared to the charging body material. For example, the support 260 may be made out of a metal and molded into a part of the charging body 252 during manufacturing. In some implementations, the support 260 may substantially extend along two opposing walls of the charging body 252 and not extend along the remaining two opposing walls, as shown in FIG. 2C. Such configuration of the support 260 may limit the direction and extent the charging body 252 may flex. For example, as shown in FIGS. 2C and 2D, a gap 262 formed between opposing sides of the support 260 may allow the charging body 252 and/or chamber 256, including one or more of the chamber walls 258, to flex. For example, the ability of the chamber 256 to flex can allow opposing chamber walls 258 to be pushed towards and away from each other, which can assist with allowing the chamber 256 to be cleaned.

In some embodiments, some or all of the charging body 252 may be made out of a material having an opacity that allows a charging light 268 along the vaporizer device 100 to illuminate therethrough. For example, a substantial part of the charging body 252 may be made out of a material having an opacity of approximately 85% to approximately 99%, such as 95%. However, one or more parts of the charging body 252 may include a different material and/or structural property to allow light to travel therethrough.

As shown in FIG. 2B, the charging body 252 may include a window 264 configured to allow light emitted from the charging light 268 to pass through the window 264. In some embodiments, the window 264 may include a through hole that extends through the chamber wall 258. In some embodiments, the window 268 may include an area along the chamber wall 258 that includes a thinner wall thickness compared to a part of the chamber wall surrounding the window 264. Additionally or alternatively, in some embodiments the window 264 can include a different material property compared to a part of the chamber wall surrounding the window 264 (e.g., less than 50% opacity). For example, the window 264 may align with a charging light 268 on an embodiment of a vaporizer body 110 when the vaporizer body 110 is coupled to the charging body 252, as shown in FIG. 2B. As such, a user may be able to observe light emitted from the charging light 268 through the window 264 thereby allowing the user to determine the charging status of the vaporizer device 100, such as while the vaporizer device 100 is charging.

As shown in FIGS. 2B and 2D, the support 260 may include a cutout 266 that aligns with the window 264 thereby allowing the charging light 268 to illuminate through the charging body 252, including the support 260. For example, the cutout 266 may include a through-hole that is sized and shaped the same as or similar to the window 264. The cutout 266 can further provide support around the window 264 to ensure the charging light 268 is aligned with the window 264, thereby allowing light from the charging light 268 to pass through the cutout 266 and window 264.

Figure 3A:
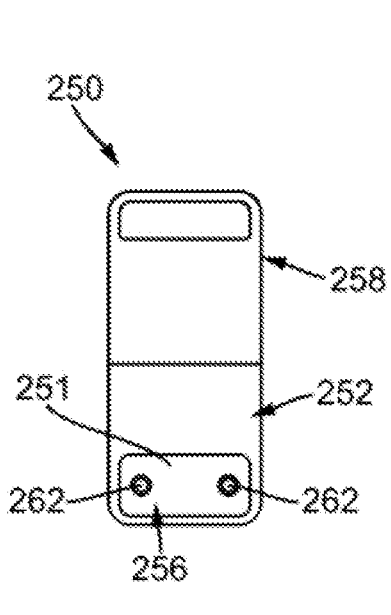
FIG. 3A depicts an example of a charging adapter consistent with implementations of the current subject matter.
Figure 3B:
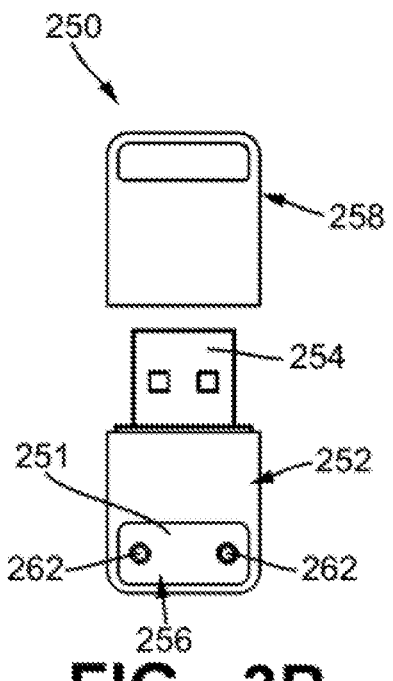
FIG. 3B depicts an example of a charging adapter consistent with implementations of the current subject matter.
Figure 3C:
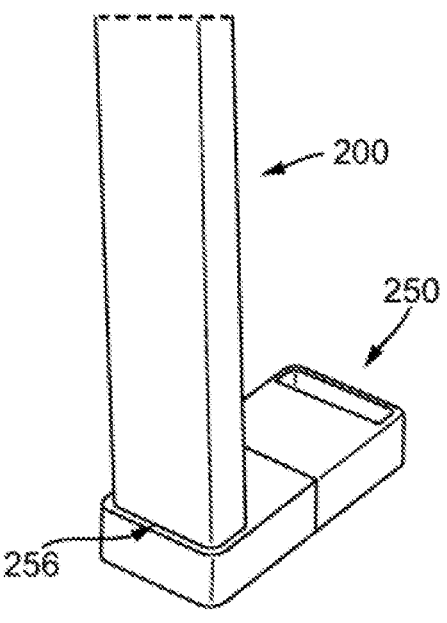
FIG. 3C depicts an example of a charging adapter consistent with implementations of the current subject matter.
Figure 3D:
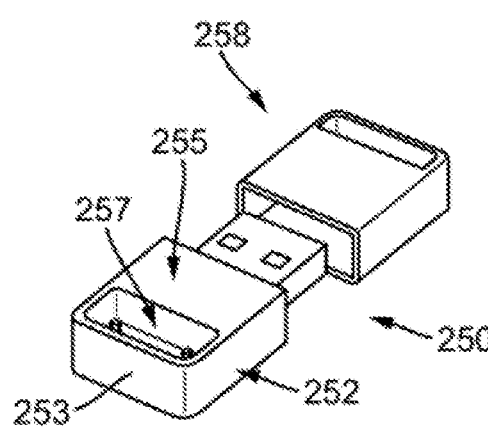
FIG. 3D depicts an example of a charging adapter consistent with implementations of the current subject matter.

FIGS. 3A-D illustrate another example of the charging adapter 250 consistent with implementations of the current subject matter. In some implementations of the current subject matter, the vaporizer device 100 may be coupled with the charging device 175 via the example of the charging adapter 250 shown in FIGS. 3A-D. In the example shown in FIGS. 3A-D, the charging adapter 250 may include the charging body 252 and a cap 258 releasably secured to the charging body 252. As shown in FIGS. 3B and 3D, the charging body 252 can include a universal serial bus (USB) feature 254 and a docking feature 256. Moreover, as shown in FIG. 3A, the cap 258 can be secured over and protect the USB feature 254 of the charging body 252, such as when the charging body 252 is not being used to charge the vaporizer device 100.

As shown in FIGS. 3B and 3D, the cap 258 can be uncoupled from the charging body 252 thereby exposing the USB feature 254. When the cap 258 is removed, the USB feature 254 can be coupled to a USB coupling feature (e.g., USB female receptacle along a computing device, power adapter, etc.) to thereby allow the charging body 252 to assist with charging the vaporizer device 100 when the vaporizer device 100 coupled thereto.

As shown in FIG. 3C, the vaporizer device 100 can be coupled to the vaporizer coupling feature 256 of the charging adapter 250. The vaporizer coupling feature 256 may include a recess 257 along the body of the charging adapter 250. The recess 257 can be shaped similar to or the same as a profile shape of the vaporizer device 100 (e.g., a charging end of the vaporizer). In some embodiments, the recess 257 is defined by a base 251 and one or more recess walls 253 extending between the base 251 and a top surface 255 of the charging body 252. For example, the recess 257 can have a rectangular shape that provides a sliding fit between the recess walls 253 and a charging end of the vaporizer device 100. As shown in FIGS. 3A and 3B, the vaporizer coupling feature 256 can include one or more charging contacts 262 positioned along the base 251 of the recess 257. For example, the charging end of the vaporizer device 100 can include one or more vaporizer charging contacts, such as the receptacle contacts 125, described above, that are in communication with the power source 112 (e.g., rechargeable battery) of the vaporizer device 100, which can align with and contact the charging contacts 262 when the charging end of the vaporizer device 100 is coupled to the vaporizer coupling feature 256.

As such, when the vaporizer device 100 is coupled to the vaporizer coupling feature 256 of the charging adapter 250, the charging contacts 262 of the charging body 252 may be aligned with and contact the cartridge contacts 124 of the vaporizer device 100, as shown in FIG. 3C. Additionally, once the USB feature 254 is coupled to an external power source (e.g., a portable device such as a smartphone, a tablet computer, a personal computer, and/or the like), the charging body 252 may provide an electrical pathway that allows the external power source to recharge the power source 112 of the vaporizer 100.

As shown in FIG. 3D, the vaporizer coupling feature 256 can be positioned along the top surface 255 of the charging body 252 and the USB feature 254 can extend from an end of the charging adapter 250, such that the USB feature 254 extends approximately ninety degrees relative to the base 251. For example, the top surface and surface along which the USB feature 254 extends from can be orthogonal relative to each other. As such, when the vaporizer device 100 is coupled to the vaporizer coupling feature 256, the vaporizer device 100 can extend approximately ninety degrees relative to the USB feature 254. This configuration can allow the vaporizer device 100 to charge while taking up minimal lateral space (e.g., desk space).

Damage to the USB feature 254, including collection of debris within and/or on the USB feature 254, can reduce the efficiency of the charging body 252 and may prevent the charging body 252 from providing the electrical pathway thus rendering the charging body 252 unusable for charging a vaporizer device 100. As such, protecting the USB feature 254 can be important for maintaining the effectiveness of the charging adapter 250, as well as prolonging the life of the charging adapter 250. As such, embodiments of the charging adapter 250 described herein include the cap 258 for at least protecting the USB feature 254. Other features and benefits may be associated with the cap 258, some of which are described herein.

Figure 4:
FIG. 4 depicts a circuit diagram illustrating an example of a charger consistent with implementations of the current subject matter.
Figure 4:
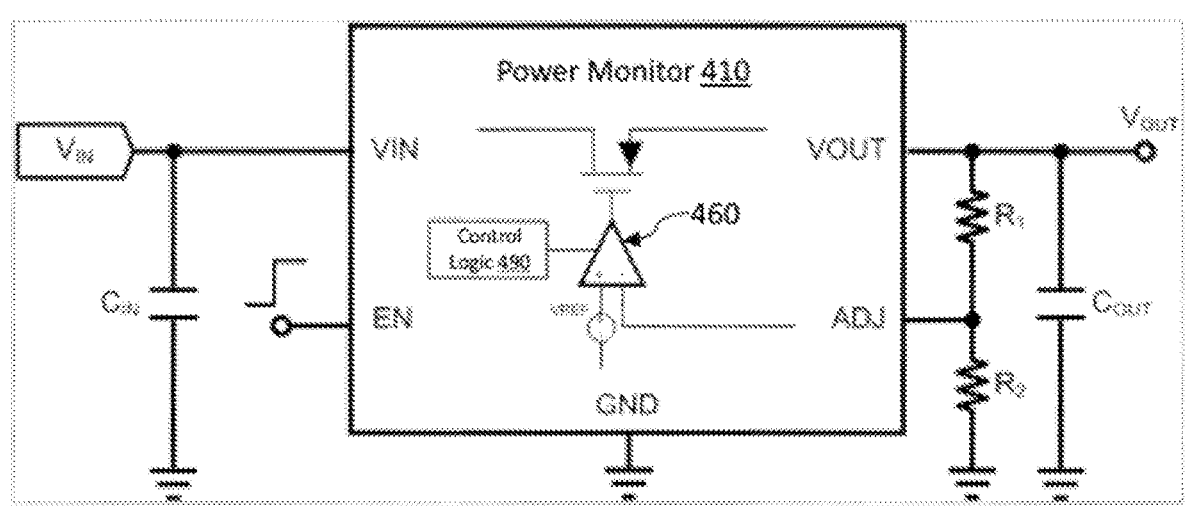

Referring again to FIG. 1D, the vaporizer device 100 may include a charger 400 configured to charge the power source 112 (e.g., a battery and/or the like) with a charging current from the charging device 175. FIG. 4 depicts a circuit diagram illustrating an example of the charger 400 consistent with implementations of the current subject matter. The charger 400 may be a linear charger (e.g., a current limited, low dropout (LDO) linear voltage regulator) that includes a power monitor 410. The charger 400 may be disposed within the vaporizer device 100 and configured to charge the power source 112 (e.g., the battery) included in the vaporizer device 100, for example, with a charging current from the charging device 175.

Although FIG. 4 does not include a current limiter, it should be appreciated that the example of the power monitor 410 shown in FIG. 4 may be configured to regulate the voltage of the charger 400. Moreover, as shown in FIG. 4, the power monitor 410 may include a differential amplifier 460 configured to determine a difference between an output voltage $V_{OUT}$ of the charger 400 and a target output voltage corresponding to the reference voltage $V_{REF}$. The power monitor 410 may include a control logic 490 configured to regulate, based at least on an output of the differential amplifier 460 indicating whether the output voltage $V_{OUT}$ of the charger 400 is equal to the target output voltage indicated by the reference voltage $V_{REF}$, the output voltage $V_{OUT}$ of the charger 400 in order to maintain the output voltage $V_{OUT}$ of the charger 400 at the target output voltage.

In order to maintain the output voltage $V_{OUT}$ of the charger 400 at the target output voltage, the power monitor 410 may reduce the input voltage $V_{IN}$ from the charging device 175 coupled to the vaporizer device 100 if, for example, the input voltage $V_{IN}$ from the charging device 175 exceeds the target output voltage indicated by the reference voltage $V_{REF}$. The presence of an excess input voltage $V_{IN}$ at the vaporizer device 100 may result in power loss at least because the excess input voltage $V_{IN}$ is dissipated as heat. The charger 400 stepping down the input voltage $V_{IN}$ from the charging device 175 may be especially electrically inefficient if the charging device 175 had stepped up the voltage of the power source 184 to provide the input voltage $V_{IN}$. As such, in some implementations of the current subject matter, the charging device 175, for example, the voltage controller 182 at the charging device 175, may be configured to maintain a predetermined voltage differential (e.g., 100 millivolts) between the input voltage $V_{IN}$ and the voltage $V_{BAT}$ of the power source 112 (e.g., a battery and/or the like) at the vaporizer device 100. In doing so, the charging device 175 may avoid an excess voltage differential between the input voltage $V_{IN}$ and the voltage $V_{BAT}$ of the power source 112 that give rise to electrical inefficiencies during the charging process.

To further illustrate, the transistor in the high current path Q1 of the power monitor 410 may regulate the output voltage $V_{OUT}$ of the charger 400 to a constant value determined by the reference voltage $V_{REF}$ and the voltage divider formed from a first resistor R1 and a second resistor R2. The power $P_h$ dissipated by the charger 400 may be expressed as Equation (1) below:

$$P_h=(V_{IN}-V_{OUT})\times I_{OUT}+V_{IN}\times I_Q \qquad (1)$$

wherein $I_Q$ may denote a quiescent current of the power monitor 410.

Equation (2) below may express the efficiency η of operating the power monitor 410 to control the output voltage $V_{OUT}$ of the charger 400 during the charging of the vaporizer device 100.

$$\eta = \frac{(P_{in}-P_h)}{P_{in}} \qquad (2)$$

wherein $P_{in}=V_{IN}\times I_{OUT}$

In a simple first order calculation, the energy delivered by a 5-V power source at the portable device for a 500 milliamps of charging current may be estimated as $P_{in}=5V\times 0.5A=2.5W$ while the average power required to charge the battery (e.g., the power source 112) of the vaporizer device 100 may be estimated as $P_{in}$=3.8V×0.5A=1.9W. Based on these estimates, the charging efficiency η of the charger 400 controlled by the power monitor 410 may be $$\eta = \frac{1.9\ W}{2.5\ W} = 76\%.$$

Contrastingly, in some implementations of the current subject matter, because the voltage controller 182 at the charging device 175 regulates the output voltage of the charging device 175 in a closed control loop, the input voltage $V_{IN}$ from the charging device 175 may be maintained at a threshold voltage (e.g., 100 millivolts) above the voltage $V_{BAT}$ of the power source 112 (e.g., a battery and/or the like) of the vaporizer device 100. That is, the voltage controller 182 at the charging device 175 may adjust the output voltage of the charging device 175 (e.g., by increasing, decreasing, or eliminating a boost applied to a voltage received from the power source 184 via a boost converter included in the charging device 175) in order to maintain a predetermined voltage differential (e.g., 100 millivolts) between the input voltage $V_{IN}$ from the charging device 175 and the voltage $V_{BAT}$ of the power source 112 (e.g., a battery and/or the like) of the vaporizer device 100.

Avoiding an excessive voltage differential between the input voltage $V_{IN}$ from the charging device 175 and the voltage $V_{BAT}$ of the power source 112 may increase the charging efficiency 77 of the charger 400 at the vaporizer device 100. For example, if the voltage $V_{BAT}$ of the battery is 3.8 volts, then the input voltage $V_{IN}$ may be adjusted to be a threshold voltage above the $V_{BAT}$ of the battery (e.g., 3.9 volts). While the average power required to charge the battery (e.g., the power source 112) of the vaporizer device 100 may remain the same (e.g., $P_{in}$=3.8V×0.5A=1.9W), the energy that is delivered in this example scenario may be $P_{in}$=3.9V×0.5A=1.95W. Accordingly, the resulting charging efficiency 77 of the charger 400 may be significantly higher at $$\eta = \frac{1.9\ W}{1.95\ W} = 97.4\%.$$

As noted, the voltage controller 182 may be configured to maintain a predetermined voltage differential between the input voltage $V_{IN}$ that the vaporizer device 100 receives from the charging device 175 and the voltage $V_{BAT}$ of the power source 112 (e.g., a battery and/or the like) at the vaporizer device 100. In some implementations of the current subject matter, the predetermined voltage differential may be configured to avoid an excess voltage differential between the input voltage $V_{IN}$ of the charger 400 and the voltage $V_{BAT}$ of the power source 112 at the vaporizer device 100. Moreover, the predetermined voltage differential may be a fixed value or a variable value subject to dynamic adjustments.

In some implementations of the current subject matter, the predetermined voltage differential may be account for other current draw that may occur during the charging of the vaporizer device 100. For example, the predetermined voltage differential may be adjusted to account for the current drawn by one or more light emitting diodes (LEDs) configured to provide feedback to a user based on a status and/or mode of operation of the vaporizer device 100. A typical light emitting diode may draw approximate 5-20 milliamps of current. While this current may be negligible compared to the overall current drawn from the charger 400 during constant current charge (e.g., approximately 400-700 milliamps), it may become more significant towards the end of the constant voltage charge when the overall current drawn from the charger decreases to approximately 10-30 milliamps.

In some implementations of the current subject matter, the input voltage $V_{IN}$ the vaporizer device 100 receives from the charging device 175 may be maintained, in a closed control loop, by the voltage controller 182 at the charging device 175 while the power source 112 (e.g., a battery and/or the like) in the vaporizer device 100 is being charged by and/or via the charging device 175. As noted, the charging device 175 may be communicatively coupled to the vaporizer device 100 in order for the vaporizer device 100 and the charging device 175 to exchange at least some data while the vaporizer device 100 is being charged by the charging device 175. For example, in some implementations of the current subject matter, the vaporizer device 100 may communicate, to the charging device 175, the current voltage $V_{BAT}$ of the power source 112 (e.g., a battery and/or the like) in the vaporizer device 100 such that the voltage controller 182 at the charging device 175 may adjust the input voltage $V_{IN}$ the vaporizer device 100 receives from the charging device 175 based on the current voltage $V_{BAT}$ of the power source 112 at the vaporizer device 100.

Various communication links may exist between the vaporizer device 100 and the charging device 175 to enable the transfer of data including, for example, serial communication based on a single-wire protocol, a two-wire protocol, and/or the like. The vaporizer device 100 and the charging device 175 may use a wireless communication protocol such as, for example, near field communication (NFC), Bluetooth, and/or the like. It should be appreciated that any single-wire protocol or two-wire protocol may be used for the serial communication link between the charging device 175 and the vaporizer device 100 including, for example, two wire universal asynchronous receiver transmitter (UART), I²C, single wire interface (SWI), serial peripheral interface (SPI), controller area network (CAN), and/or the like. Alternatively and/or additionally, the serial communication may occurs via the contacts 128 of the vaporizer device 100 coupled with the contacts 190 of the charging device 175 in order to obviate the need for additional pins the vaporizer device 100 and/or the charging device 175. The serial communication may occur via the contacts 128 of the vaporizer device 100 coupled with the contacts 190 in the charging device 175 with or without disrupting the charge current flowing through the contacts 128 and the contacts 190.

Figure 5:
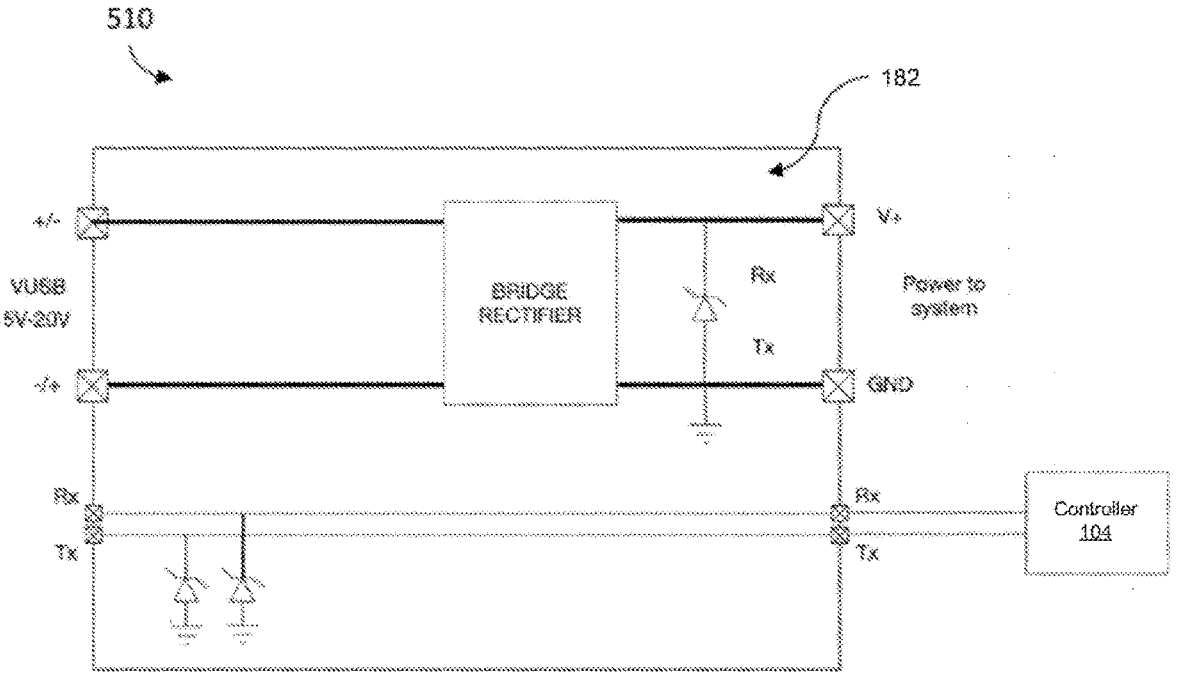
FIG. 5 depicts a block diagram illustrating an example of a serial communication system consistent with implementations of the current subject matter.

FIG. 5 depicts a block diagram illustrating an example of a serial communication system 510 consistent with implementations of the current subject matter. Referring to FIG. 5, the serial communication system 510 may be a two wire universal asynchronous receiver transmitter (UART) system having a transmitter (Tx) pin and a receiver (Rx) pin at the charging device 175, for example, the voltage controller 182, that are configured to exchange data with the vaporizer device 100, for example, the controller 104 of the vaporizer device 100. According to some implementations of the current subject matter, the charging device 175 (e.g., the voltage controller 182) may receive, from the vaporizer device 100 (e.g., the controller 104), a value corresponding to the current voltage $V_{BAT}$ of the power source 112 (e.g., a battery and/or the like) in the vaporizer device 100. While the vaporizer device 100 is being charged by and/or via the charging device 175, the charging device 175 may be configured to adjust, based at least on the current voltage $V_{BAT}$ of the power source 112 at the vaporizer device 100, the input voltage $V_{IN}$ that the vaporizer device 100 receives from the charging device 175. For example, the charging device 175 may adjust the input voltage $V_{IN}$ to the vaporizer device 100 such that the input voltage $V_{IN}$ to the vaporizer device 100 is no more than a threshold voltage above the current voltage $V_{BAT}$ of the power source 112 at the vaporizer device 100.

Figure 6:
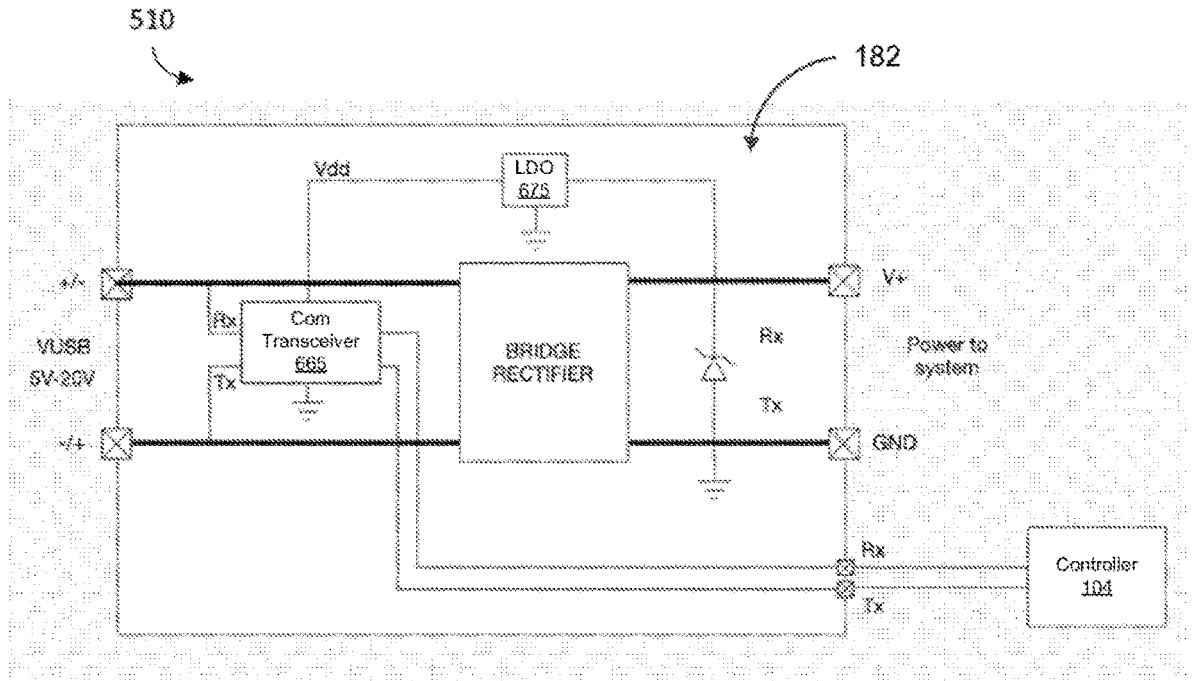
FIG. 6 depicts a block diagram illustrating another example of a serial communication system consistent with implementations of the current subject matter.

Alternatively, the serial communication between the vaporizer device 100 and the charging device 175 may be conducted via the contacts 128 of the vaporizer device 100 coupled with the contacts 190 in the charging device 175. FIG. 6 depicts a block diagram illustrating another example of the serial communication system 510 in which the serial communication between the vaporizer device 100 and the charging device 175 is conducted via the contacts 128 of the vaporizer device 100 coupled with the contacts 196 in the charging device 175. The example of the serial communication system 510 shown in FIG. 6 may further include a communication transceiver 665 and a low dropout regulator (LDO) 675. In some implementations of the current subject matter, in order for the serial communication between the vaporizer device 100 and the charging device 175 to be conducted via the contacts 128 of the vaporizer device 100 coupled with the contacts 190 in the charging device 175, the charging device 175, for example, the voltage controller 182, may monitor the current flowing to the vaporizer device 100. When the current drops below a minimum charge current by a threshold voltage, the charging device 175 may set the input voltage $V_{IN}$ of the vaporizer device 100 below a minimum voltage $V_{BAT}$ of the power source 112 at the vaporizer device 100 (e.g., 2.5 volts or 1.8 volts) and utilize this lower voltage for exchanging data with the vaporizer device 100, for example, the controller 104.

In other implementations of the current subject matter, the controller 104 at the vaporizer device 100 may control the charge current from the charging device 175 and modulate the load current from the charging device 175. Meanwhile, the charging device 175, for example, the voltage controller 182, may monitor the current flowing to the vaporizer device 100. The vaporizer device 100 may set two levels of load current, which may be monitored by the charging device 175 to establish the communication link between the charging device 175 and the vaporizer device 100. Once the communication link is established, the charging device 175 may respond by lowering the output voltage of the charging device 175 below the minimum charging voltage (e.g., 2.5V or 1.8V) such that the lower voltage across the contacts 128 of the vaporizer device 100 coupled with the contacts 190 may be used to transmit data to the vaporizer device 100.

In some implementations of the current subject matter, the charging device 175 may include a boost converter configured to increase the voltage of the power source 184 to a voltage that is capable of charging the power source 112 at the vaporizer device 100. Moreover, in examples of the charging device 175 having a system processor, the charging device 175 may include a digital-to-analog converter (DAC) or a pulse-width modulated (PWM) digital potentiometer with resistor-capacitor (RC) filtering. Alternatively, the charging device 175 may include a resistive divider configured to provide multiple discrete output voltages.

Figure 7:
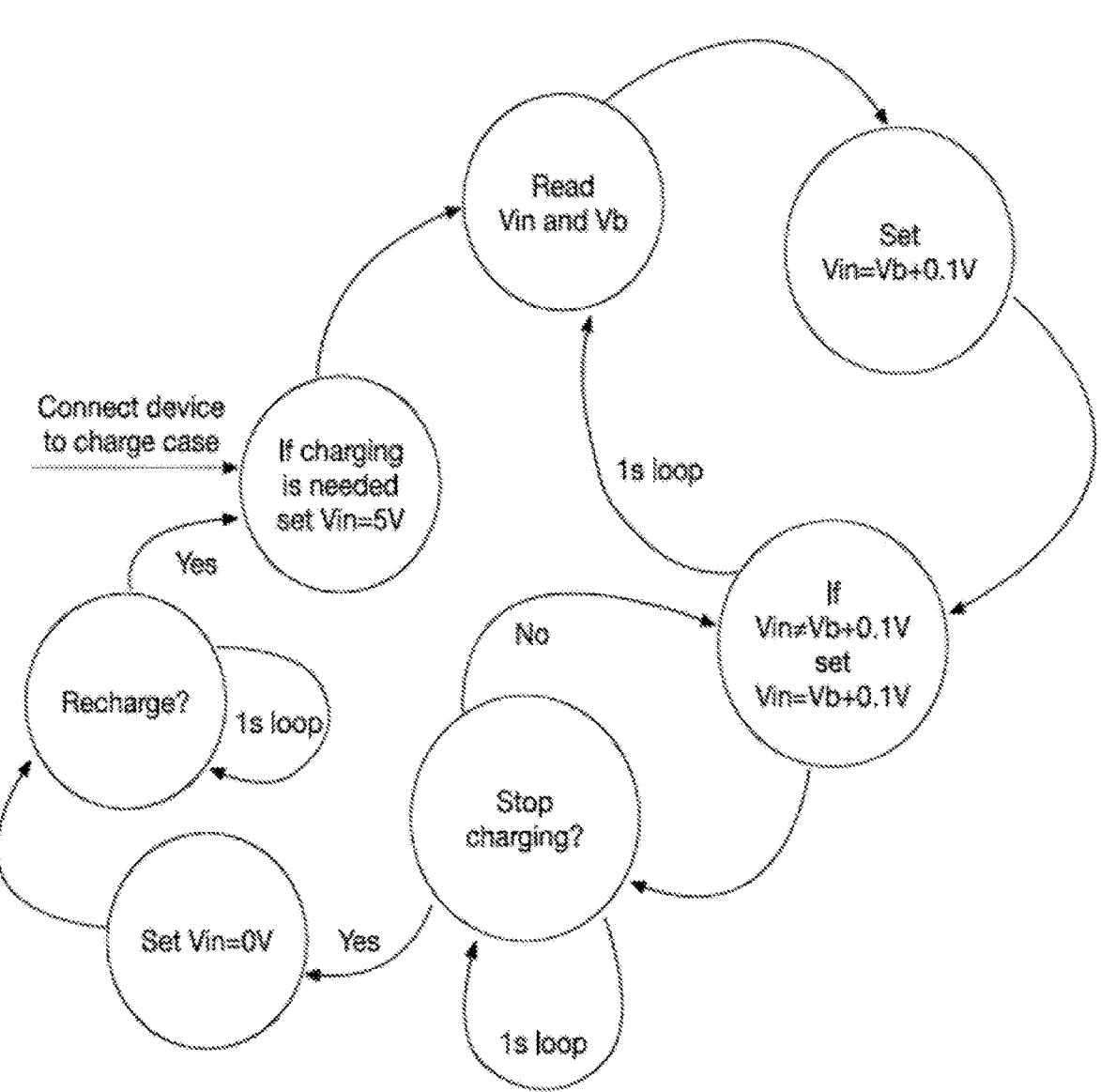
FIG. 7 depicts a state diagram illustrating an example of a control loop consistent with implementations of the current subject matter.

FIG. 7 depicts a state diagram illustrating an example of a control loop consistent with implementations of the current subject matter. As shown in FIG. 7, when the vaporizer device 100 is coupled with the charging device 175 and the charging device 175 determines that the vaporizer device 100 requires charging, the charging device 175 may initially set the input voltage $V_{IN}$ of the vaporizer device 100 to a first voltage. The first voltage may correspond to the output voltage $V_{OUT}$ of the charging device 175. Moreover, the first voltage may be higher than the what is needed to charge the power source 112 (e.g., a battery and/or the like) at the vaporizer device 100. In instances where the first voltage exceeds the voltage of the power source 184, a boost converter at the charging device 175 may increase an output voltage of the power source 184 to the first voltage.

As shown in FIG. 7, the charging device 175 may monitor the input voltage $V_{IN}$ at the vaporizer device 100 and the voltage $V_{BAT}$ of the power source 112 at the vaporizer device 100. For example, the charging device 175 may measure, at regular time intervals (e.g., once every second), the input voltage $V_{IN}$ at the vaporizer device 100 and the voltage $V_{BAT}$ of the power source 112 at the vaporizer device 100 and set the input voltage $V_{IN}$ of the vaporizer device 100 to a second voltage.

In some implementations of the current subject matter, the second voltage may be a threshold voltage (e.g., 0.1 volts) above the voltage $V_{BAT}$ of the power source 112 (e.g., a battery and/or the like) at the vaporizer device 100 if the input voltage $V_{IN}$ at the vaporizer device 100 does not equal the voltage $V_{BAT}$ of the power source 112 at the vaporizer device 100. The second voltage may be a threshold voltage higher than $V_{BAT}$ of the power source 112 t the vaporizer device 100 in order to enable the charging of the vaporizer device 100. However, to minimize power loss, it should be appreciated that the voltage differential between the second voltage and the voltage $V_{BAT}$ of the battery at the vaporizer device 100 may be the minimal quantity necessary to enable the charging of the vaporizer device 100. In instances where the second voltage exceeds the voltage of the power source 184, the boost converter at the charging device 175 may increase the output voltage of the power source 184 to the second voltage.

Further as shown in FIG. 7, the charging device 175 may be configured to determine whether to stop the charging of the vaporizer device 100. In the event the charging device 175 determines to stop the charging of the vaporizer device 100, the charging device 175 may be configured to set the input voltage $V_{IN}$ of the vaporizer device 100 to a third voltage (e.g., 0 volts).

Figure 8:
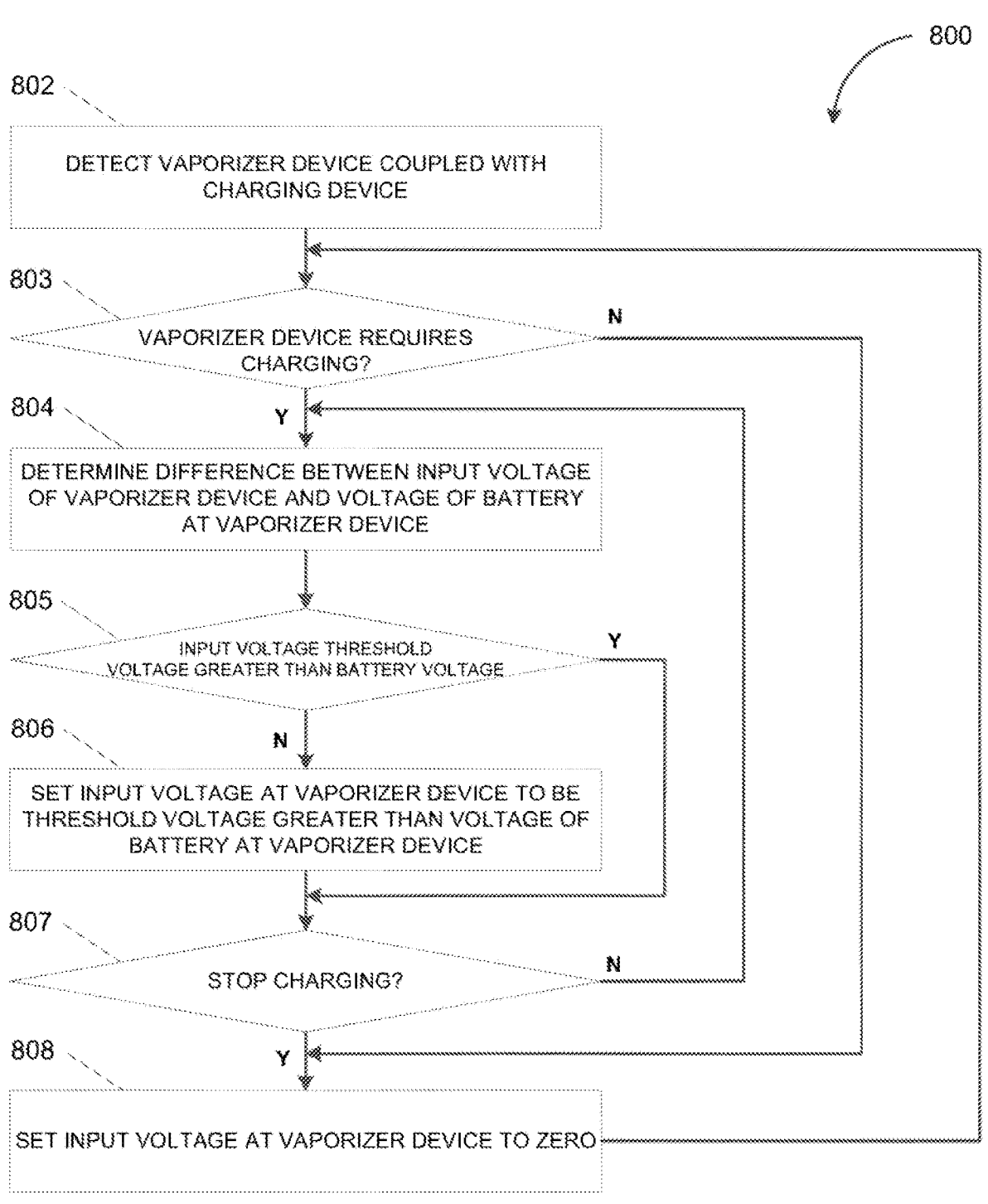
FIG. 8 depicts a flowchart illustrating a process for charging a vaporizer device consistent with implementations of the current subject matter.

FIG. 8 depicts a flowchart illustrating a process 800 for charging a vaporizer device consistent with implementations of the current subject matter. Referring to FIGS. 1A-C, 2A-F, 3A-D, 5-6, and 7-8, the process 800 may be performed by the charging device 175 in order to charge an electronic device including, for example, the vaporizer device 100.

The charging device 175 may detect the vaporizer device 100 coupled with the charging device 175 (802). For example, the charging device 175 may detect the vaporizer device 100 being coupled to the charging device 175 based at least on a presence (or absence) of a signal across the contacts 190 of the charging device 175, which are configured to couple with the contacts 128 of the vaporizer device 100.

The charging device 175 may determine whether the vaporizer device 100 requires charging (803). For example, the charging device 175 may determine that the vaporizer device 100 requires charging based on a quantity of current flowing to the vaporizer device 100. A below threshold current flowing to the vaporizer device 100 may indicate that the power source 112 (e.g., a battery and/or the like) at the vaporizer device 100 is fully charged and does not require charging.

The charging device 175 may determine that the vaporizer device 100 does not require charging (803-N). In the event the charging device 175 determines that the vaporizer device 100 does not require charging, the charging device 175 may set the input voltage at the vaporizer device 100 to zero (808). Moreover, the process 800 may resume at operation 803 and the charging device 175 may continue to determine whether the vaporizer device 100 requires charging.

Alternatively, in response to determining that the vaporizer device 100 requires charging (803-Y), the charging device 175 may determine an input voltage of the vaporizer device 100 and a voltage of the power source 112 at the vaporizer device 100 (804). For example, the charging device 175 may determine the input voltage $V_{IN}$ at the vaporizer device 100. Moreover, the charging device 175 may communicate (e.g., via a serial communication link) data with the vaporizer device 100 that includes one or more indications of the current voltage $V_{BAT}$ of the power source 112 (e.g., a battery and/or the like) at the vaporizer device 100 and/or a desired voltage requested by the vaporizer device 100.

The charging device 175 may determine whether the input voltage at the vaporizer device 100 is a threshold voltage above than the voltage of the power source 112 at the vaporizer device 100 (805). For example, the charging device 175 may determine whether the input voltage $V_{IN}$ at the vaporizer device 100 is a threshold voltage (e.g., 0.1 volts) greater than the voltage $V_{BAT}$ of the power source 112 (e.g., a battery and/or the like) at the vaporizer device 100.

If the charging device 175 determines that the input voltage at the vaporizer device 100 is not the threshold voltage above the voltage of the power source 112 at the vaporizer device 100 (805-N), the charging device 175 may set the input voltage at the vaporizer device 100 to be the threshold voltage above the voltage of the power source 112 at the vaporizer device 100 (806). For example, the charging device 175 may set the input voltage $V_{IN}$ at the vaporizer device 100 to be the threshold voltage (e.g., 0.1 volts) greater than the voltage $V_{BAT}$ of the power source 112 (e.g., a battery and/or the like) at the vaporizer device 100 if the charging device 175 determines that the input voltage $V_{IN}$ at the vaporizer device 100 is not the threshold voltage (e.g., 0.1 volts) greater than the voltage $V_{BAT}$ of the power source 112 at the vaporizer device 100. In order to set the input voltage $V_{IN}$ at the vaporizer device 100 to be the threshold voltage (e.g., 0.1 volts) greater than the voltage $V_{BAT}$ of the power source 112, the charging device 175, for example, the boost converter at the charging device 175, may be configured to increase the voltage of the power source 184 at the charging device 175. For instance, the boost converter at the charging device 175 may increase the voltage of the power source 184 if the voltage of the power source 184 does not exceed the voltage $V_{BAT}$ of the power source 112 by the threshold voltage (e.g., 0.1 volts).

Moreover, the charging device 175 may determine whether to stop charging the vaporizer device 100 (807). For instance, the charging device 175 may determine whether to stop charging the vaporizer device 100 based on the quantity of current flowing to the vaporizer device 100. As noted, a below threshold current flowing to vaporizer device 100 may indicate that the power source 112 (e.g, a battery and/or the like) at the vaporizer device 100 is fully charged. Accordingly, the charging device 175 may determine to stop charging the vaporizer device 100 in response to detecting a below threshold current flowing to the vaporizer device 100.

Alternatively, the charging device 175 may determine that the input voltage at the vaporizer device 100 is the threshold voltage greater than the voltage of the power source 112 at the vaporizer device 100 (805-Y). Accordingly, the process 800 may resume at operation 807 and the charging device 175 may again determine again determine whether to stop charging the vaporizer device 100.

In the event the charging device 175 determines to stop charging the vaporizer device 100 (807-Y), the charging device 175 may set the input voltage at the vaporizer device 100 to zero (808). For example, as noted, the charging device 175 may determine to stop charging the vaporizer device 100 in response to detecting a below threshold current flowing to the vaporizer device 100. The process 800 may then resume at operation 803 and the charging device 175 may again determine, for example, based on the quantity of current flowing to the vaporizer device 100, whether the vaporizer device 100 requires charging. Alternatively, the charging device 175 may determine to not stop charging the vaporizer device 100 (807-N). As such, the process 800 may resume at operation 804 and the charging device 175 may again determine the input voltage $V_{IN}$ at the vaporizer device 100 and the voltage $V_{BAT}$ of the power source 112 (e.g., a battery and/or the like) at the vaporizer device 100 before determining whether the input voltage $V_{IN}$ at the vaporizer device 100 is the threshold voltage greater than the voltage $V_{BAT}$ of the power source 112 (e.g., a battery and/or the like) at the vaporizer device 100.

Terminology

When a feature or element is herein referred to as being "on" another feature or element, it can be directly on the other feature or element or intervening features and/or elements can also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements can be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature can have portions that overlap or underlie the adjacent feature.

Terminology used herein is for the purpose of describing particular embodiments and implementations only and is not intended to be limiting. For example, as used herein, the singular forms "a," "an," and "the" are intended to include the plural forms as well, unless the context clearly indicates otherwise.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device can be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers can be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value can have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes can be made to various embodiments without departing from the teachings herein. For example, the order in which various described method steps are performed may often be changed in alternative embodiments, and in other alternative embodiments, one or more method steps may be skipped altogether. Optional features of various device and system embodiments may be included in some embodiments and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system can include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Use of the term "based on," herein and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described herein can be directed to various combinations and subcombinations of the disclosed features and/or combinations and subcombinations of several further features disclosed herein. In addition, the logic flows depicted in the accompanying figures and/or described herein do not necessarily require the particular order shown, or sequential order, to achieve desirable results. Other implementations may be within the scope of the following claims.

What is claimed is:

1. An apparatus, comprising:
a controller configured to at least:
receive data indicating a voltage associated with a battery of a vaporizer device, wherein the data indicating the voltage associated with the battery of the vaporizer device includes one or more indicators of a current voltage of the battery;
output, to the vaporizer device, power at an output voltage determined based at least in part on the data indicating the voltage associated with the battery of the vaporizer device;
determine a difference between an input voltage at the vaporizer device and the current voltage of the battery of the vaporizer device; and
in response to determining that the difference is below a threshold voltage, set the input voltage of the vaporizer device to be at least the threshold voltage greater than the current voltage of the battery of the vaporizer device.

2. The apparatus of claim 1, wherein the threshold voltage is from 0.05 volts to 0.2 volts.

3. The apparatus of claim 1, wherein the threshold voltage is 0.1 volts.

4. The apparatus of claim 1, wherein the data indicating the voltage of associated with the battery of the vaporizer device includes one or more indicators of a desired voltage requested by the vaporizer device.

5. The apparatus of claim 4, wherein the desired voltage requested by the vaporizer device is the threshold voltage above the current voltage of the battery of the vaporizer device.

6. The apparatus of claim 1, wherein the controller is further configured to:
detect that the vaporizer device is coupled with the apparatus; and
in response to detecting that the vaporizer device is coupled with the apparatus, determine whether the battery of vaporizer device requires charging,
wherein the apparatus outputs power to the vaporizer device in response to determining that the vaporizer device requires charging.

7. The apparatus of claim 6, wherein the apparatus determines that the vaporizer device requires charging based at least on a current flowing to the vaporizer device being above a threshold current.

8. The apparatus of claim 1, wherein the vaporizer device and the apparatus are coupled via a serial communication system, and wherein the data indicating the voltage associated with the battery of the vaporizer device is transmitted from the vaporizer device to the apparatus via the serial communication system.

9. The apparatus of claim 8, wherein the serial communication system comprises a universal asynchronous receiver transmitter system including a transmitter pin and a receiver pin.

10. The apparatus of claim 8, wherein the data indicating the voltage associated with the battery of the vaporizer device is transmitted via one or more charging contacts at the vaporizer device and one or more corresponding charging contacts at the apparatus.

11. The apparatus of claim 10, wherein the controller is further configured to:
respond to a current flowing to the vaporizer device being below a threshold current by at least setting the input voltage of the vaporizer device below a minimum voltage of the battery of the vaporizer device for communicating the data indicating the voltage of the battery of the vaporizer device.

12. The apparatus of claim 1, wherein the controller is further configured to:
determine whether to stop charging the vaporizer device;
in response to determining that charging of the vaporizer device will be stopped, discontinue the output of power to the vaporizer device; and
in response to determining that charging of the vaporizer device will continue, continue to output power to the vaporizer device.

13. The apparatus of claim 1, wherein the apparatus comprises a power bank, a portable charging case, or a charging adapter.

14. A charging device, comprising:
a power source;
at least one charging contact; and
a controller coupled to the power source and the at least one charging contact, the controller configured to:
receive, from an electronic device and via the at least one charging contact, data indicating a voltage associated with a battery of the electronic device, wherein the data indicating the voltage associated with the battery of the electronic device includes one or more indicators of a current voltage of the battery;

output, to the electronic device and via the at least one charging contact, power at an output voltage that is based on the voltage associated with the battery of the electronic device;

determine a difference between an input voltage at the electronic device and the current voltage of the battery of the electronic device; and in response to determining that the difference is below a threshold voltage, set the input voltage of the electronic device to be at least the threshold voltage greater than the current voltage of the battery of the electronic device.

15. A vaporizer device, comprising:

a battery;

at least one charging contact; and a controller coupled to the battery and the at least one charging contact, the controller configured to:

transmit, to a charging device and via the at least one charging contact, data indicating a voltage associated with the battery, wherein the voltage associated with the battery comprises a current voltage of the battery;

receive, from the charging device and via the at least one charging contact, power at an input voltage that is based on the voltage associated with the battery;

determine the voltage associated with the battery by adding a voltage differential to a current voltage of the battery; and charge the battery with the power.

16. The vaporizer device of claim 15, wherein the voltage associated with the battery comprises a voltage requested by the controller in order to charge the battery.

17. The vaporizer device of claim 15, wherein the voltage associated with the battery is less than 5 volts.

18. The vaporizer device of claim 14, wherein the threshold voltage is from 0.05 volts to 0.2 volts.

19. The vaporizer device of claim 14, wherein the data indicating the voltage associated with the battery of the vaporizer device includes one or more indicators of a desired voltage requested by the vaporizer device.

20. The vaporizer device of claim 19, wherein the desired voltage requested by the vaporizer device is the threshold voltage above the current voltage of the battery of the vaporizer device.

21. The apparatus of claim 14, wherein the controller is further configured to:

detect that the electronic device is coupled with the charging device; and in response to detecting that the electronic device is coupled with the charging device, determine whether the battery of the electronic device requires charging, wherein the charging device outputs power to the electronic device in response to determining that the electronic device requires charging.

* * * * *